US010406288B2

United States Patent
Reber et al.

(10) Patent No.: US 10,406,288 B2
(45) Date of Patent: Sep. 10, 2019

(54) DELIVERY MECHANISM FOR AN AUTOINJECTOR

(75) Inventors: Dominic Charles Reber, Cambridge (GB); Congyi Huang, Cambridge (GB); Matthew Young, Cambridge (GB)

(73) Assignee: OVAL MEDICAL TECHNOLOGIES LIMITED, Cambridge (GB)

( * ) Notice: Subject to any disclaimer, the term of this patent is extended or adjusted under 35 U.S.C. 154(b) by 922 days.

(21) Appl. No.: 13/989,551

(22) PCT Filed: Dec. 1, 2011

(86) PCT No.: PCT/GB2011/052378
§ 371 (c)(1),
(2), (4) Date: Aug. 9, 2013

(87) PCT Pub. No.: WO2012/073035
PCT Pub. Date: Jun. 7, 2012

(65) Prior Publication Data
US 2014/0046259 A1    Feb. 13, 2014

(30) Foreign Application Priority Data
Dec. 2, 2010 (GB) .................................. 1020475.8

(51) Int. Cl.
*A61M 5/20* (2006.01)

(52) U.S. Cl.
CPC ..... *A61M 5/2033* (2013.01); *A61M 2005/206* (2013.01); *A61M 2005/2013* (2013.01); *A61M 2205/581* (2013.01)

(58) Field of Classification Search
CPC .. A61M 5/3157; A61M 5/2033; A61M 5/326; A61M 5/5086; A61M 2005/2073;
(Continued)

(56) References Cited

U.S. PATENT DOCUMENTS

| 4,642,099 A | 2/1987 | Phillips et al. |
| 6,099,503 A | 8/2000 | Stradella |

(Continued)

FOREIGN PATENT DOCUMENTS

| CN | 1901957 A | 1/2007 |
| CN | 101282756 A | 10/2008 |

(Continued)

OTHER PUBLICATIONS

International Preliminary Report on Patentability from corresponding PCT/GB2011/052378 dated Jun. 13, 2013.
(Continued)

*Primary Examiner* — Nathan R Price
*Assistant Examiner* — Justin L Zamory
(74) *Attorney, Agent, or Firm* — Lando & Anastasi, LLP

(57) ABSTRACT

The invention provides a delivery mechanism for an autoinjector comprising: a first drive member configured to drive a first component in an axial direction; a second drive member configured to drive a second component in an axial direction; and a release mechanism configured to control a sequence of release of the first drive member and the second drive member, wherein the release mechanism is positioned at least partially within the first or second drive member.

18 Claims, 24 Drawing Sheets

(58) Field of Classification Search
CPC .... A61M 2005/2013; A61M 2005/206; A61M 2005/208; A61M 2205/581
See application file for complete search history.

(56) References Cited

U.S. PATENT DOCUMENTS

| | | | |
|---|---|---|---|
| 7,500,963 B2 | 3/2009 | Westbye et al. | |
| 7,749,195 B2 | 7/2010 | Hommann | |
| 7,806,866 B2 | 10/2010 | Hommann et al. | |
| 2001/0005781 A1 | 6/2001 | Bergens et al. | |
| 2008/0195056 A1* | 8/2008 | Bishop | A61M 5/2033 604/218 |
| 2011/0218500 A1* | 9/2011 | Grunhut | A61M 5/2033 604/228 |
| 2012/0220954 A1* | 8/2012 | Cowe | A61M 5/2033 604/228 |
| 2013/0190721 A1 | 7/2013 | Kemp et al. | |
| 2013/0190722 A1 | 7/2013 | Kemp et al. | |

FOREIGN PATENT DOCUMENTS

| | | |
|---|---|---|
| CN | 101541362 A | 9/2009 |
| JP | 2005518877 A | 6/2005 |
| JP | 2008508950 A | 3/2008 |
| JP | 2008229344 A | 10/2008 |
| WO | 200024441 A1 | 5/2000 |
| WO | 2004047890 A1 | 6/2004 |
| WO | 2005023342 A1 | 3/2005 |
| WO | 2009007229 A1 | 1/2009 |
| WO | 2009063030 A1 | 5/2009 |
| WO | 2011048422 A2 | 4/2011 |

OTHER PUBLICATIONS

English Translation of Second Office Action of the State Intellectual Property of the People's Republic of China from corresponding CN Application Serial No. 201180064514.8 dated Jul. 20, 2015.
English Translation of Notices of Reasons for Rejection of the Japanese Patent Office from corresponding JP Application Serial No. 2013-541429 dated Nov. 17, 2015.
English Translation of Third Office Action of the State Intellectual Property of the People's Republic of China from corresponding CN Application Serial No. 201180064514.8 dated Mar. 8, 2016.

* cited by examiner

DELIVERY MECHANISM FOR AN AUTOINJECTOR

FIELD OF THE INVENTION

This invention relates to devices for drug storage and drug administration to a patient. In particular the invention relates to mechanisms for automated administration of a dose of drug to a patient.

BACKGROUND TO THE INVENTION

One type of drug delivery device known in the art is an autoinjector which contains a medical, therapeutic, diagnostic, pharmaceutical or cosmetic compound (drug) before it is administered, and which is used to administer the compound through the skin of the patient via a hollow needle. Autoinjectors may be used by the patient themselves or by a different user, and are also used to administer drugs to animals.

Autoinjectors are typically used because they reduce the amount of training and effort needed by a user compared with that needed for a syringe, by automating either or both processes of inserting the needle into the patient and expelling the drug through the needle. They can also reduce the fear of injection by hiding the needle from the patient.

Some autoinjectors use a single spring to provide the motive power to both insert the needle into the patient and deliver the drug. Examples of this approach include the EpiPen autoinjector from Meridian and the Humira autoinjector from Abbot.

Where an autoinjector includes only one spring to provide the force to drive both functions, the force that the spring provides for one of the functions may be higher than needed, to enable the spring to provide sufficient force for the other function. Advantageously the two functions happen one after another rather than simultaneously in order that the drug is delivered only after the needle is correctly positioned. Because the force provided by a spring typically reduces as the spring delivers energy, the spring inevitably provides a higher force for driving the first function, i.e. needle insertion, than for the following function i.e. drug delivery, whether or not this is desirable. The strength of the spring is determined by the requirement for the spring to be able to provide sufficient force and energy at every point during the drug delivery process. This often means that much higher force than is needed or desirable is provided during the needle insertion phase.

However some autoinjectors use two separate springs within their operating mechanisms to provide the motive power to insert the needle and deliver the drug. Examples of this approach are described in U.S. Pat. Nos. 4,642,099 and 7,749,195.

Where an autoinjector includes two springs, the force provided by each spring can be tailored to better suit the requirements of each function. The overall maximum stored spring force required in the autoinjector mechanism can be significantly reduced, because each spring on its own no longer needs to provide sufficient energy to drive both functions.

The use of two springs in this way typically requires an interlock mechanism to coordinate the sequence of the two functions so that significant drug is not expelled through the needle before the needle is inserted correctly into the patient. The interlock mechanism typically adds size and complexity to the autoinjector.

It is an object of the present invention to provide an improved mechanism to control the sequence of release of two drive members, such as springs, within an autoinjector, which allows the size and complexity of the autoinjector to be kept to a minimum.

SUMMARY OF THE INVENTION

Aspects of the present invention are defined in the appended independent claims, to which reference should be made. The various aspects of the invention may be provided alone or in combination with one or more of the other aspects. Preferred features of the invention are defined in the dependent claims.

The use of two drive members, such as springs, in an autoinjector, instead of just one, can provide various benefits including those listed below:
  The level of pain and distress perceived by the user can be reduced due to lower needle insertion speeds and reduced noise and shock during drug delivery.
  The risk of breakage of the drug container within the autoinjector can be reduced because of the lower maximum spring force required. This is of particular benefit where the drug container within the autoinjector consists of a relatively fragile glass syringe or cartridge.
  The cost and size of the device can be reduced because one spring can be positioned within the other, and because a reduction in the maximum spring force can allow smaller autoinjector mechanisms. Reduced size makes the autoinjector more portable, which in turn increases the likelihood that a patient will carry it with them and therefore have it available if it is needed to treat an emergency condition.

In one aspect the present invention provides a release mechanism to control the sequence of release of two drive members, such as springs, within an autoinjector, but which allows the size of the autoinjector to be kept to a minimum. It also provides accurate control of a sequence of needle insertion and drug delivery, and allows the number of components and cost of the autoinjector to be minimised. This is achieved by providing the release mechanism at least partially within the drive members.

Many existing autoinjectors typically have a mechanism mounted on the opposite end of the autoinjector from the needle which engages with one or more of the springs to prevent accidental activation of the autoinjector. This can take the form of a button or removable safety cap. For this reason the interlock mechanism to control the sequence of needle insertion and drug delivery is typically mounted on the outside of one or more of the springs. These interlock mechanisms therefore generally have the disadvantage that they add to the size and complexity of the autoinjector. In contrast, the present invention allows for a release mechanism to be positioned at least partially inside a drive member. This minimises the size of the autoinjector.

In a first aspect, a delivery mechanism for an autoinjector comprises: a first drive member configured to drive a first component; a second drive member configured to drive a second component; and a release mechanism configured to control a sequence of release of the first drive member and the second drive member, wherein the release mechanism is positioned at least partially within the first or second drive member.

Preferably, the release mechanism is positioned at least partially within both the first and the second drive member.

Typically, the first and second drive members are configured to drive the first and second components in the same direction, but it is possible for them to be different directions. For example the second direction may be parallel but opposite to the first direction.

The first drive member may be a helical spring. The second drive member may be a helical spring. Helical springs can be placed one within the other to provide a stable and compact delivery mechanism.

Preferably, one of the first and second drive members is mainly responsible for providing a force to insert a needle into a subject, and the other of the first and second drive members is mainly responsible for providing a force to expel a drug through the needle. However, the separate actions of the drive members may or may not correlate exactly with the separate functions of inserting the needle to the patient and delivering the drug; in other words, one drive member may provide the force needed for all of one function and part of the other, whereas the other drive member may provide only part of the force needed for the other function.

In one embodiment, the release mechanism comprises a locking surface, the locking surface being fixed to, or part of, the main body; and an inner retaining component configured to retain the second drive member until the locking surface is moved a predetermined distance relative to the inner retaining component, after which the second drive member is released; wherein release of the first drive member moves the inner retaining component relative to the locking surface in order to release the second drive member. This provides a robust, stable and compact release mechanism.

The inner retaining component may comprise a latch which engages on a bearing surface on the first component. The locking surface may maintain the latch in an engaged position with the bearing surface before the first drive member is released. The latch may be fixed to or part of the second component.

In use, the first drive member moves from an initial position before it is released to a final position after it has been released, and the second drive member moves from an initial position before it is released to a final position after it has been released. The mechanism may comprise a noise-generating mechanism configured to generate a sound when the first and second drive members have moved to their final positions. The noise generating mechanism informs a user when drug delivery has been successfully completed.

The noisegenerating mechanism may be positioned at least partially, and preferably fully, within the first or second drive member. This allows the device to be made compact. The noisegenerating mechanism is preferably positioned at least partially within both the first and second drive members.

The release mechanism is preferably part of an autoinjector. The autoinjector may comprise a drug container and a plunger within the drug container, and the second component may be a pusher configured to push the plunger within the drug container to deliver a drug.

The autoinjector may comprise a drug container containing a drug to be dispensed, and the first component may be fixed to the drug container so that it is not displaced relative to the drug container when the second drive member is released.

In another aspect, the invention provides a system for releasing a locking device that prevents the activation of the delivery mechanism, the releasing system being provided at a front end of the drug container, where the front end is the end to which the needle is attached and which is closest to the patient in use. This provides further opportunities to reduce the size, and in particular the width, of the overall device. It also allows for a simplified user interface which can be easier to use than that found on most autoinjectors available on the market.

In this aspect an autoinjector may comprise: a housing; a drug container having a front end coupled to a needle; a releasable drive mechanism coupled to a rear end of the drug container, in use the drive mechanism moving from a initial configuration to a final configuration to move the drug container and needle relative to the housing in order to insert the needle into a subject; and a releasable locking mechanism retaining the drive mechanism in the initial configuration, the locking mechanism being fixed to the housing and engaging the front end of the drug container.

The locking mechanism may comprise a resilient arm fixed relative to the housing.

The releasable locking mechanism may be coupled to a skin sensor configured to sense a skin surface of a subject. The skin sensor may comprise a movable element that moves relative to the housing when it is pressed against a skin surface, movement of the movable element releasing the locking mechanism from engagement with the front end of the drug container. The movable element may be configured to be in contact with the locking mechanism when the locking mechanism is engaged with front end of the drug container.

BRIEF DESCRIPTION OF THE DRAWINGS

Examples of the present invention will now be described in detail with reference to the accompanying drawings, in which:

FIG. 9b is a section view of FIG. 9a;

FIG. 10b shows a section view of FIG. 10a;

DETAILED DESCRIPTION

Figure 1A:
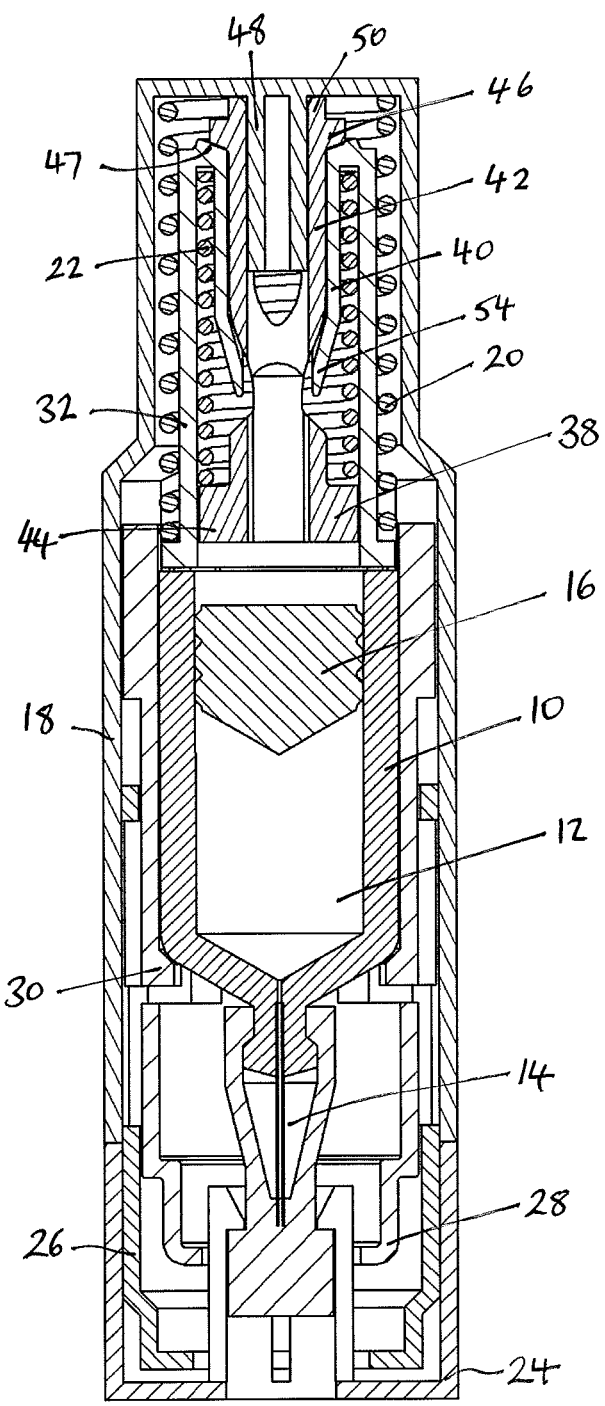
FIG. 1a shows a longitudinal crosssection of a first embodiment of an autoinjector before administration of the drug to the patient.

FIG. 1a shows a longitudinal crosssection of an autoinjector in accordance with a first embodiment of the invention, before administration of the drug to the patient.

Figure 1B:
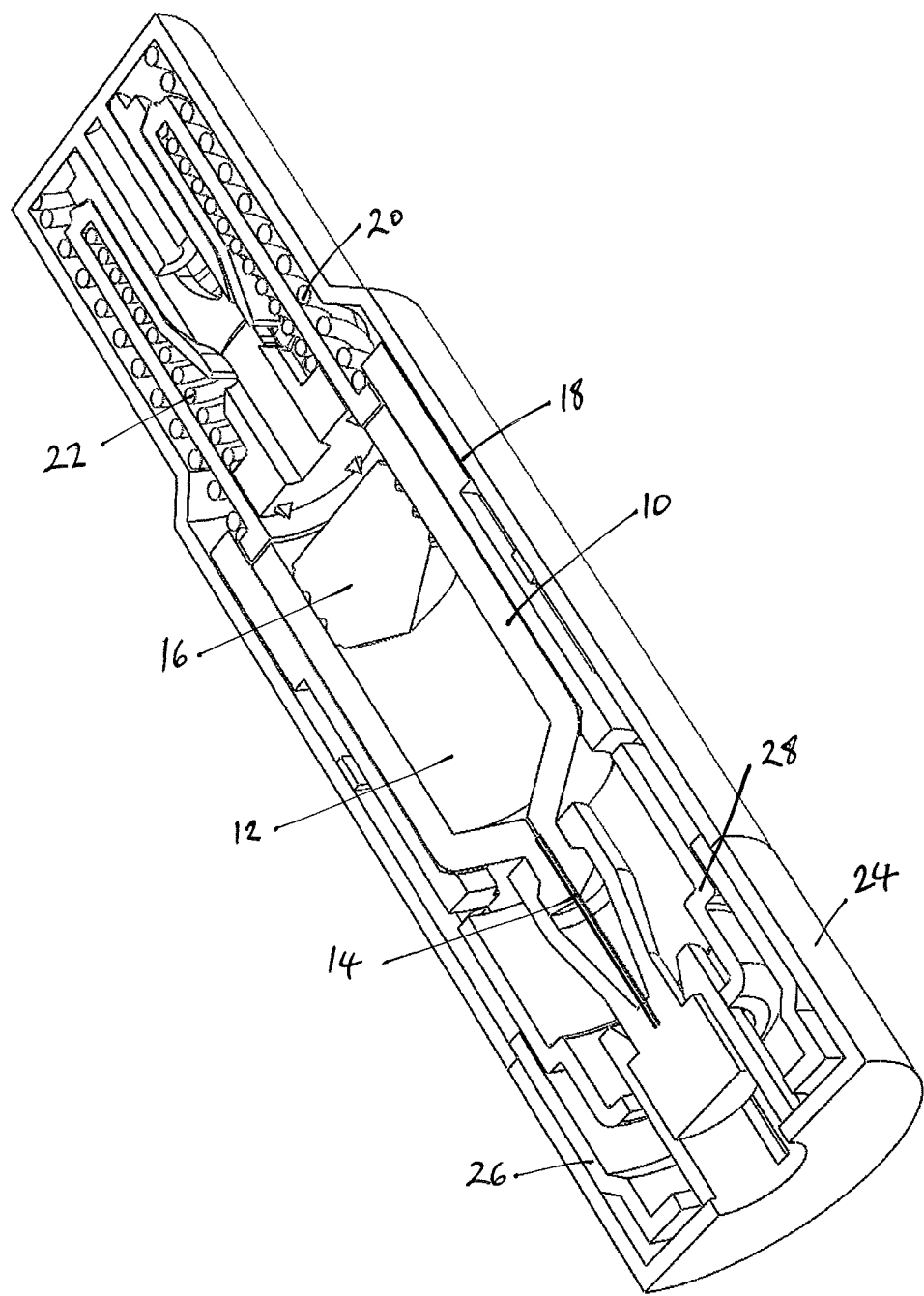
FIG. 1b shows the section view of the autoinjector of FIG. 1a from a different perspective.

FIG. 1b shows the section view of the autoinjector of FIG. 1a from a different perspective. The autoinjector comprises a drug container 10 in which a dose of drug 12 is contained. A hollow hypodermic needle 14 is fixed to a front end of the drug container 10 and a plunger 16 provided within the drug container 10. Movement of the plunger 16 towards the needle 14 causes the drug to be expelled from the drug container through the needle. As used herein "front" refers to the end of the drug container or autoinjector closest to the patient in use, i.e. the end through which the drug is delivered to the patient.

This basic syringe assembly is housed within a housing 18 that contains drive mechanisms for inserting the needle 14 into a subject and for moving the plunger 16 within the drug container 10 to expel the drug 12. The housing also contains a skin sensing mechanism for activating the drive mechanisms on contact with the skin of a subject and a noise generating mechanism to indicate to a user when delivery of the drug has been completed.

The drive mechanism comprises two springs, one for inserting the needle and one for moving the plunger. In this example, helical springs formed from metal are used. However, it should be clear that other forms of spring may be used, such as gas springs or indeed any suitable mechanical drive incorporating a resilient member that can store potential energy to be subsequently released for driving the needle or plunger, and in any combination.

The helical springs are arranged one within the other, in a coaxial relationship. However, it is not essential that they are coaxial, nor that they nest within each other, but there are advantages to both these features. The outer spring 20 is used for driving the drug container 10 and needle 14 forward through the housing 18 to insert the needle into a subject. The inner spring 22 is used to drive the plunger within the drug container to expel the drug 12 through the needle. However, in other embodiments the roles may be reversed with an inner spring driving the needle and an outer spring driving a plunger.

The sequence of operation of the two springs 20 and 22 will now be described. FIGS. 1a and 1b show the autoinjector in an initial state as it is delivered to an end user. The autoinjector includes a needle cover 24 for safety, which must be removed prior to use of the autoinjector.

Figure 2A:
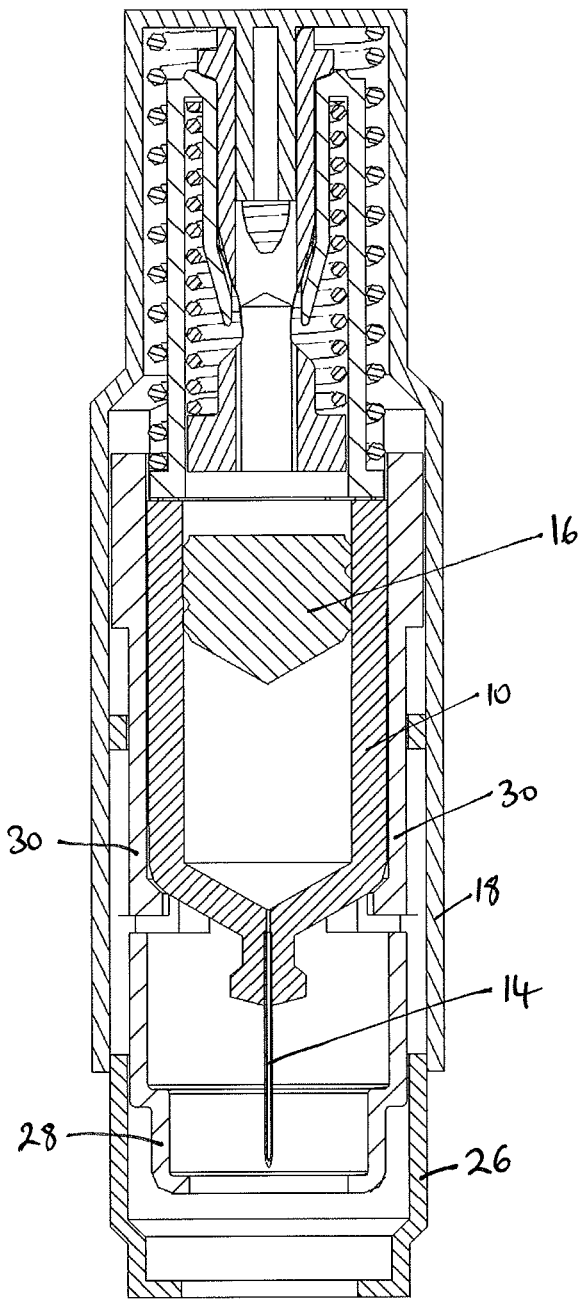
FIG. 2a shows the same autoinjector after the needle cover has been removed.
Figure 2B:
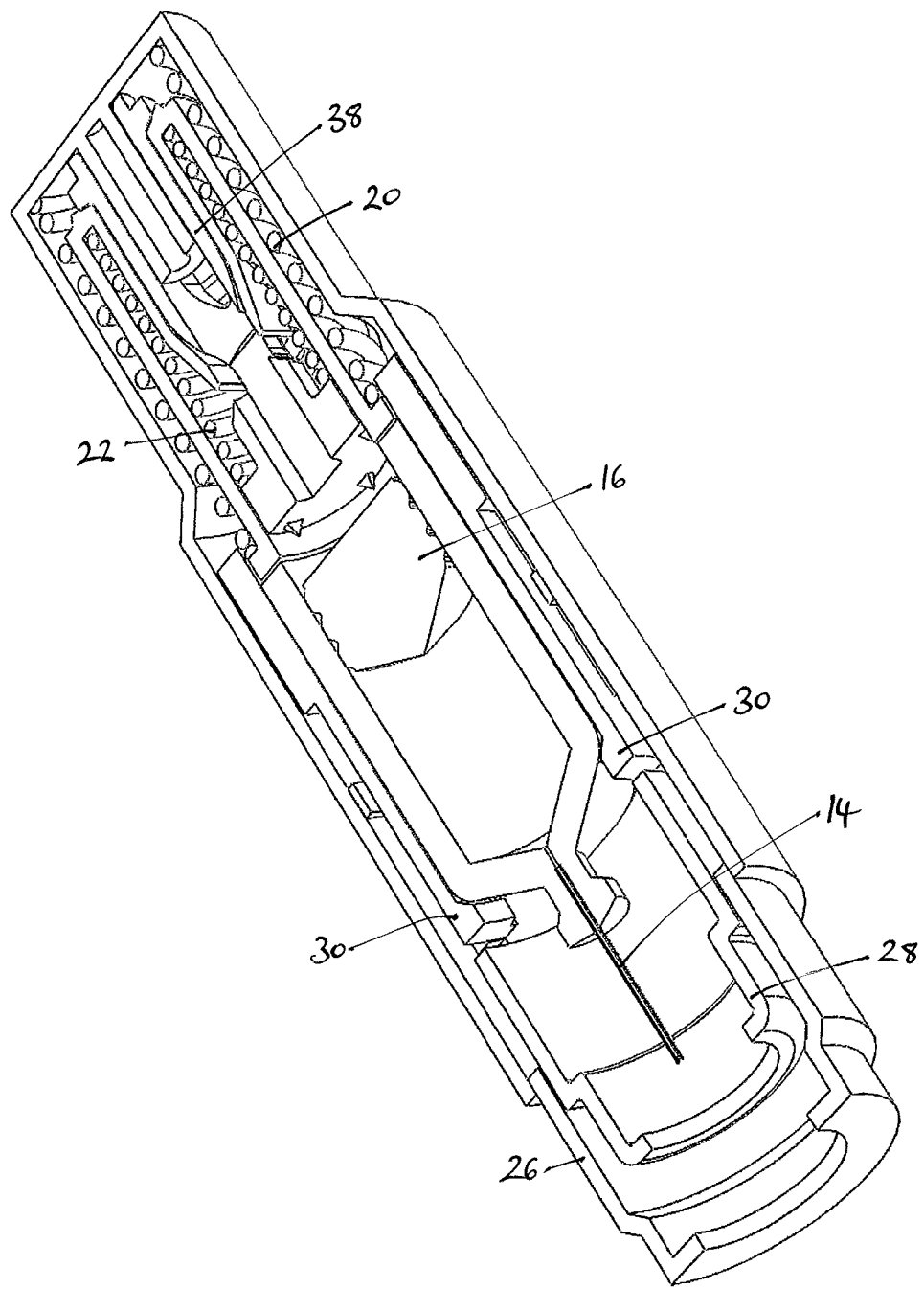
FIG. 2b shows the section view of FIG. 2a from a different perspective.
Figure 3A:
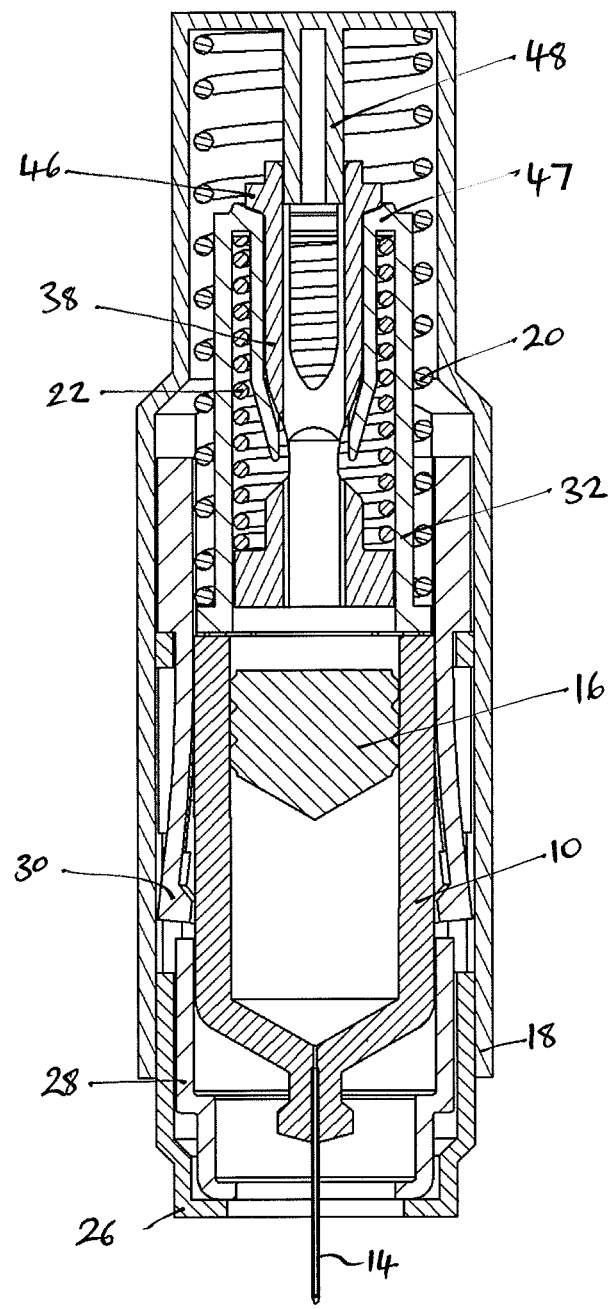
FIG. 3a shows the same autoinjector in the process of inserting the needle into the patient.
Figure 3B:
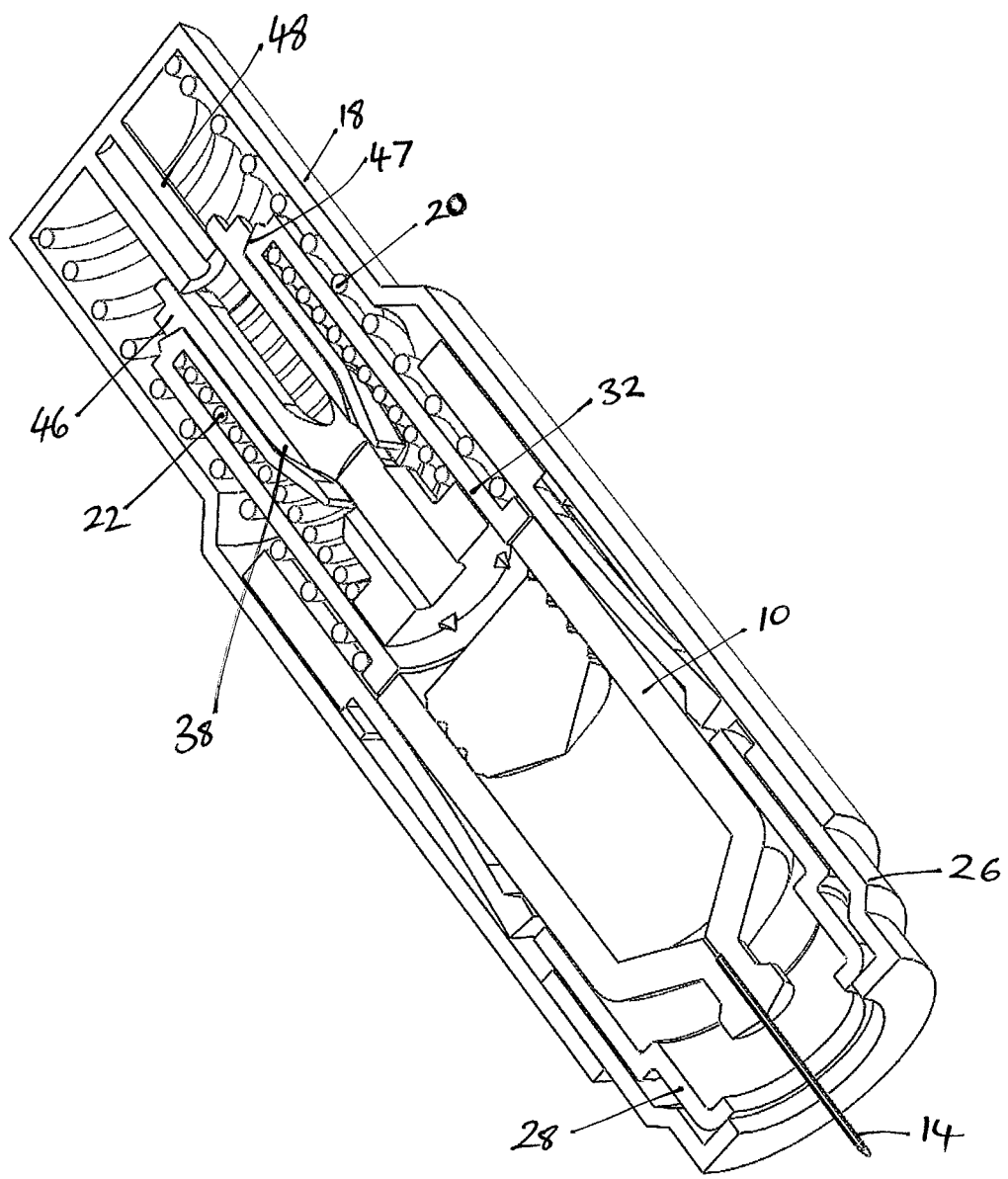
FIG. 3b shows the section view of FIG. 3a from a different perspective.

The needle cover 24 can be simply pulled off by a user or caregiver to expose the skin sensor 26. FIGS. 2a and 2b show the autoinjector with the needle cover 24 removed. The skin sensor 26, which extends beyond the front end of the housing, is placed against the skin of a subject in a position where the drug is to be injected. Application of pressure to the body of the autoinjector towards the skin surface pushes the skin sensor 26 back relative to the autoinjector housing 18. The needle 14 is still covered by a front end housing 28, so the user applied pressure does not directly cause the needle 14 to be inserted through the skin. Instead the skin sensor acts as a trigger. The needle 14 and drug container 10 are retained relative to the front end housing 28 by needle insertion latches 30 that engage a front end of the drug container 10. Once the skin sensor is pushed back a predetermined distance the needle insertion latches 30 are released, as is explained in detail with reference to FIGS. 14 to 18. Once the needle insertion latches 30 are disengaged from the drug container 10, the outer spring 20 pushes the drug container 10 and needle 14 forward through the housing 18 to insert the needle into the patient. This is illustrated in FIGS. 3a and 3b.

Figure 9A:
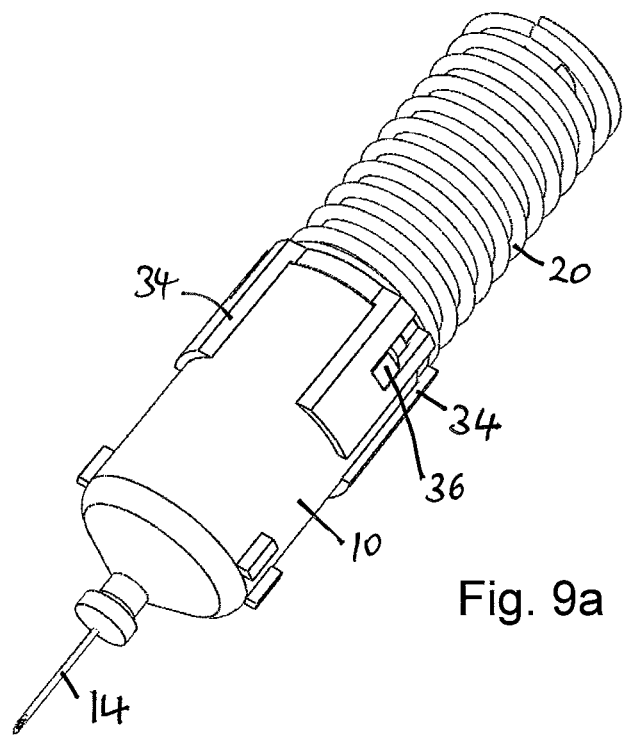
FIG. 9a shows the drug container coupled to the drive mechanism from the autoinjector of FIG. 1.
Figure 9B:
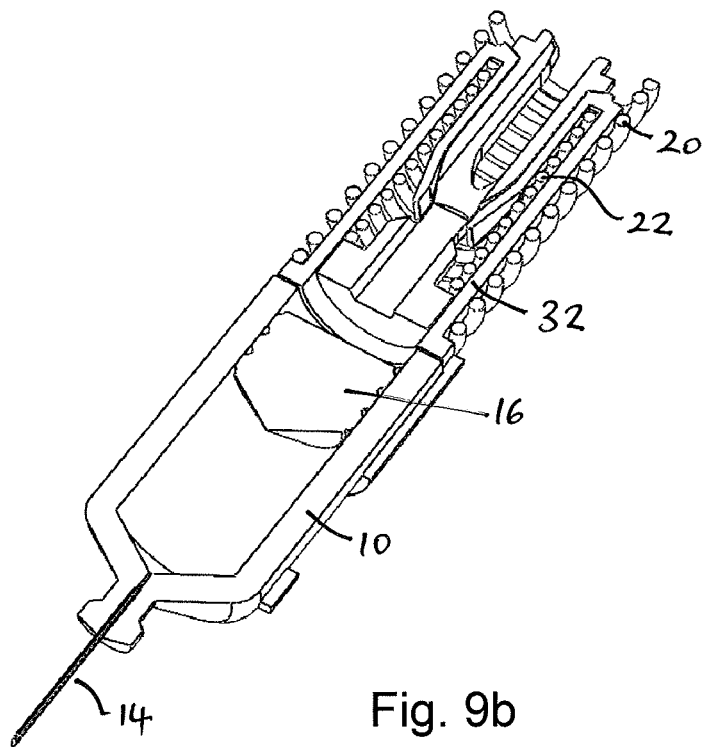

The outer spring 20 is positioned between the main housing 18 and a first component 32, in this embodiment referred to as outer spring component 32. The outer spring component is coupled to the drug container, as can be seen more clearly in FIGS. 9a and 9b. The outer spring component 32 comprises engaging arms 34 that engage with lugs 36 formed on an outer surface of the drug container 10. However, any suitable means of engagement between the outer spring component and the drug container 10 may be used, or simply abutment of the outer spring component 32 against the drug container 10.

Figure 10A:
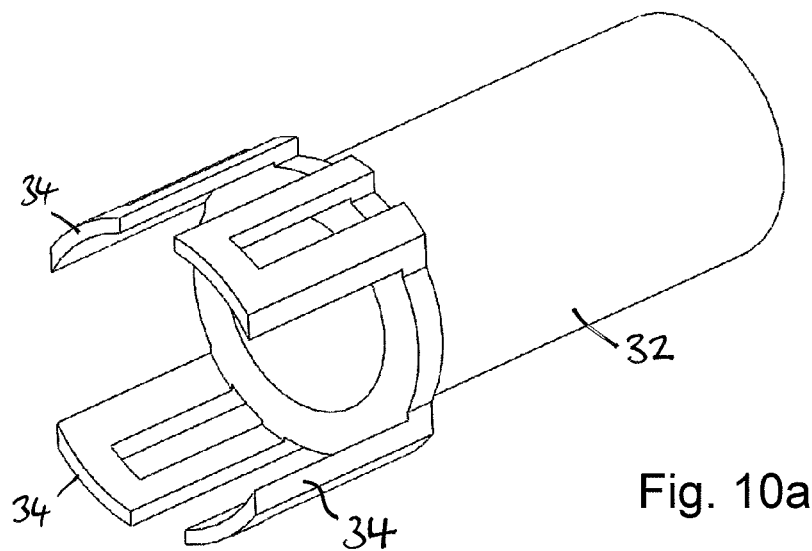
FIG. 10a shows the outer spring component.
Figure 10B:
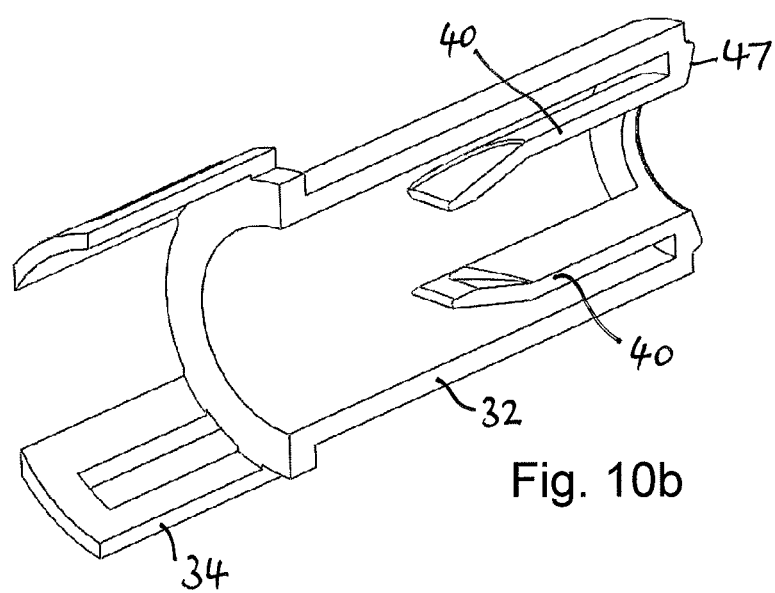
Figure 11A:
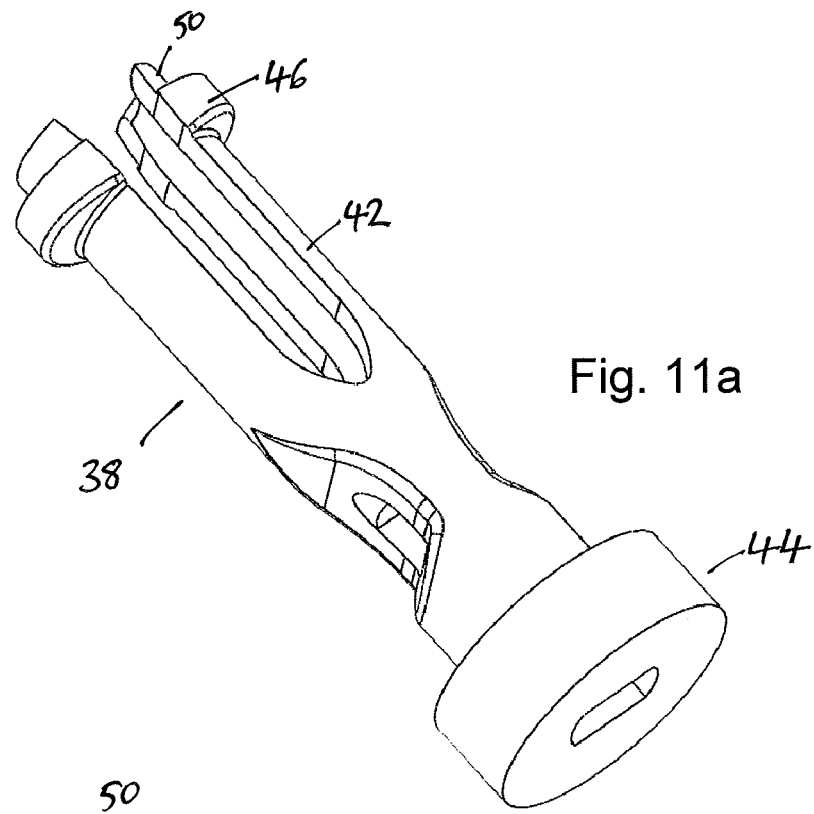
FIG. 11a shows the inner spring component.
Figure 11B:
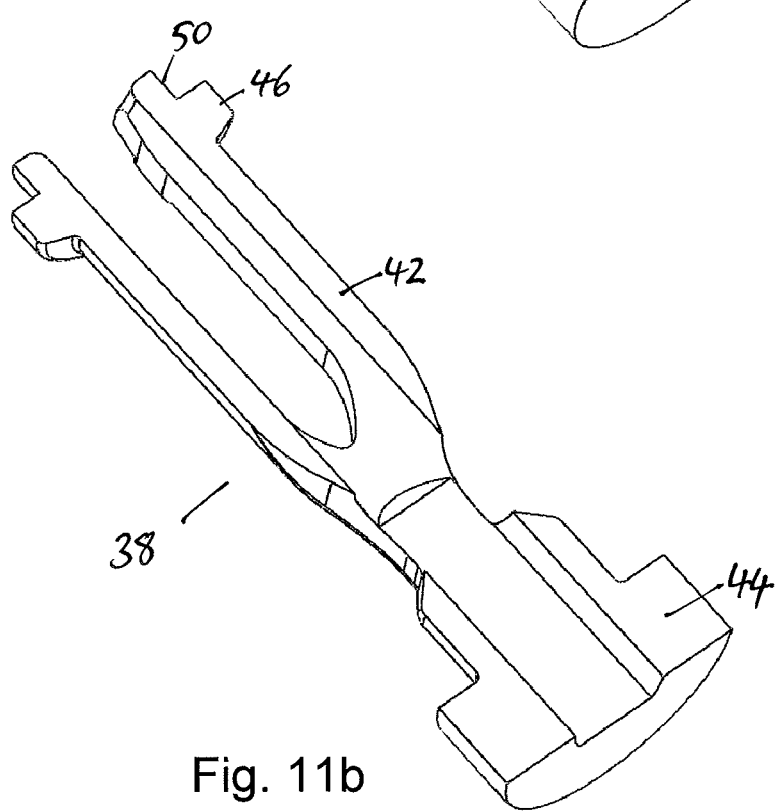
FIG. 11b shows a section view of FIG. 11b.

The outer spring component 32 moves with the drug container 10 as the needle 14 is inserted. The inner spring 22 is held between the outer spring component 32 and a second component 38, in this embodiment also referred to as an inner spring component 38. The inner spring component acts on the plunger during expulsion of the drug. But the outer spring component 32 retains the inner spring 22 in a compressed condition until the needle is partially or fully inserted. The outer spring component 32 extends around the inner spring 22, over a back side of the inner spring, and has leg portions 40 positioned within the inner spring. The leg potions 40 are clearly illustrated in FIG. 10b. The inner spring component 38 comprises a front end pusher portion 44 that engages with the plunger, as will be described with reference to FIGS. 5a and 5b. The inner spring component 38 also comprises an inner retaining component in the form of inner resilient leg portions 42 that include inner spring retaining lobes 46 at their back ends. The inner resilient leg portions are pressed outwardly by a locking surface 48 that is part of (or rigidly fixed to) the main housing so that retaining lobes 46 engage with an inner spring retaining surface 47 on the outer spring component 32 and are prevented from disengagement by the locking surface 48. In this way the inner spring is locked in a compressed state, and moves with the outer spring component 32, until the retaining lobes 46 can be released from the inner spring retaining surface 47.

Once the outer spring is released by the needle insertion latches 30, it drives the outer spring component 32 down through the housing. The locking surface 48 is dimensioned so that the inner resilient leg portions 42 disengage with the locking surface 48 as or just before the drug container 10 reaches the end of its travel within the main housing 18, i.e. as the outer spring reaches its fullest extension. As soon as the inner resilient leg portions 42 are disengaged from the locking surface 48, the lobes 46 disengage from the retaining surface 47. This disengagement is due to the action of the inner spring 22.

Figure 4A:
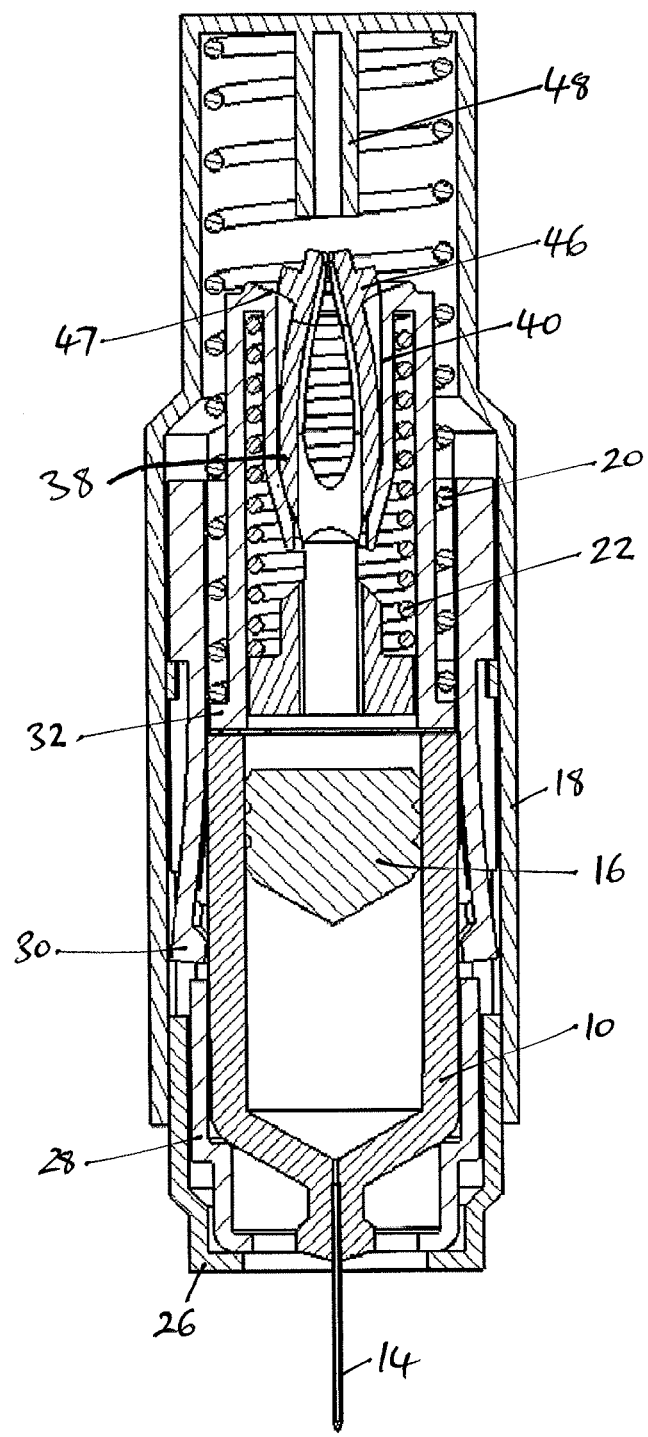
FIG. 4a shows the same autoinjector with the needle fully extended and the second spring released so that it can expel the drug into the patient.
Figure 4B:
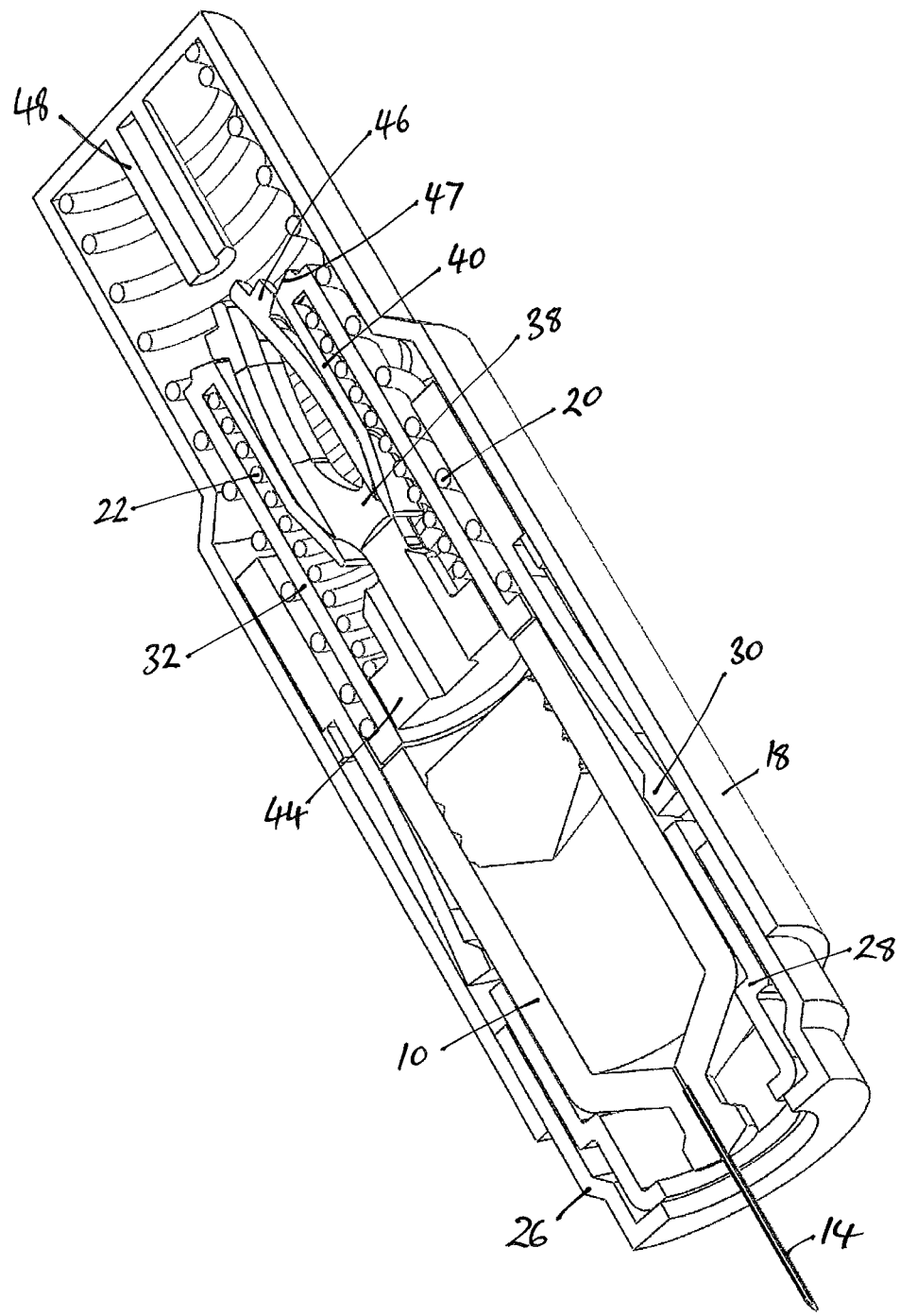
FIG. 4b shows the section view of FIG. 4a from a different perspective.
Figure 5A:
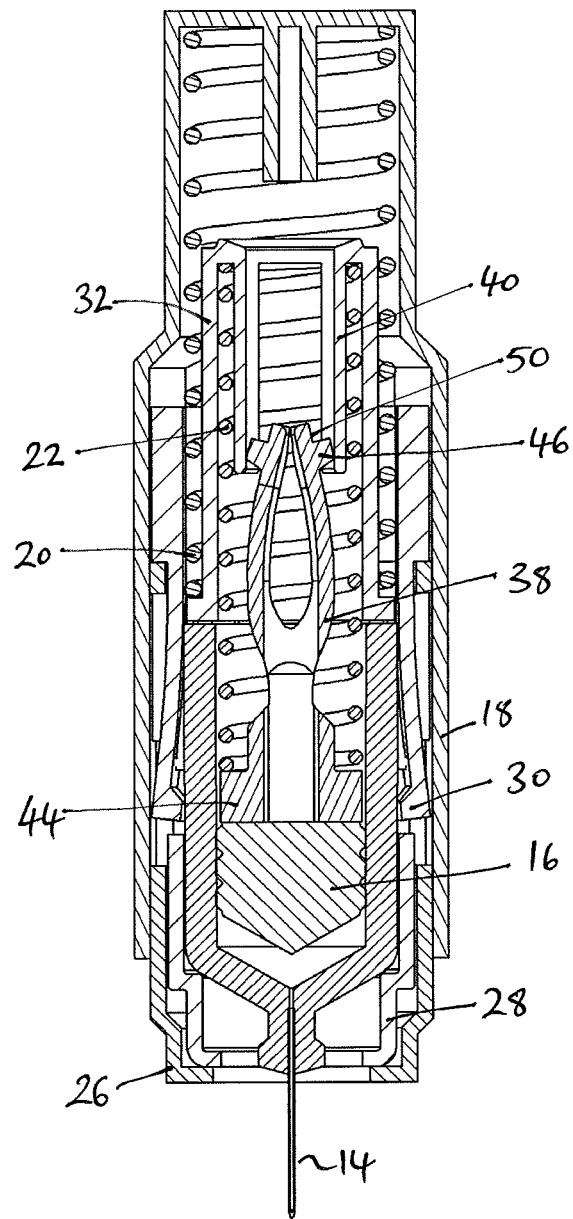
FIG. 5a shows the same autoinjector as the drug is being expelled.
Figure 5B:
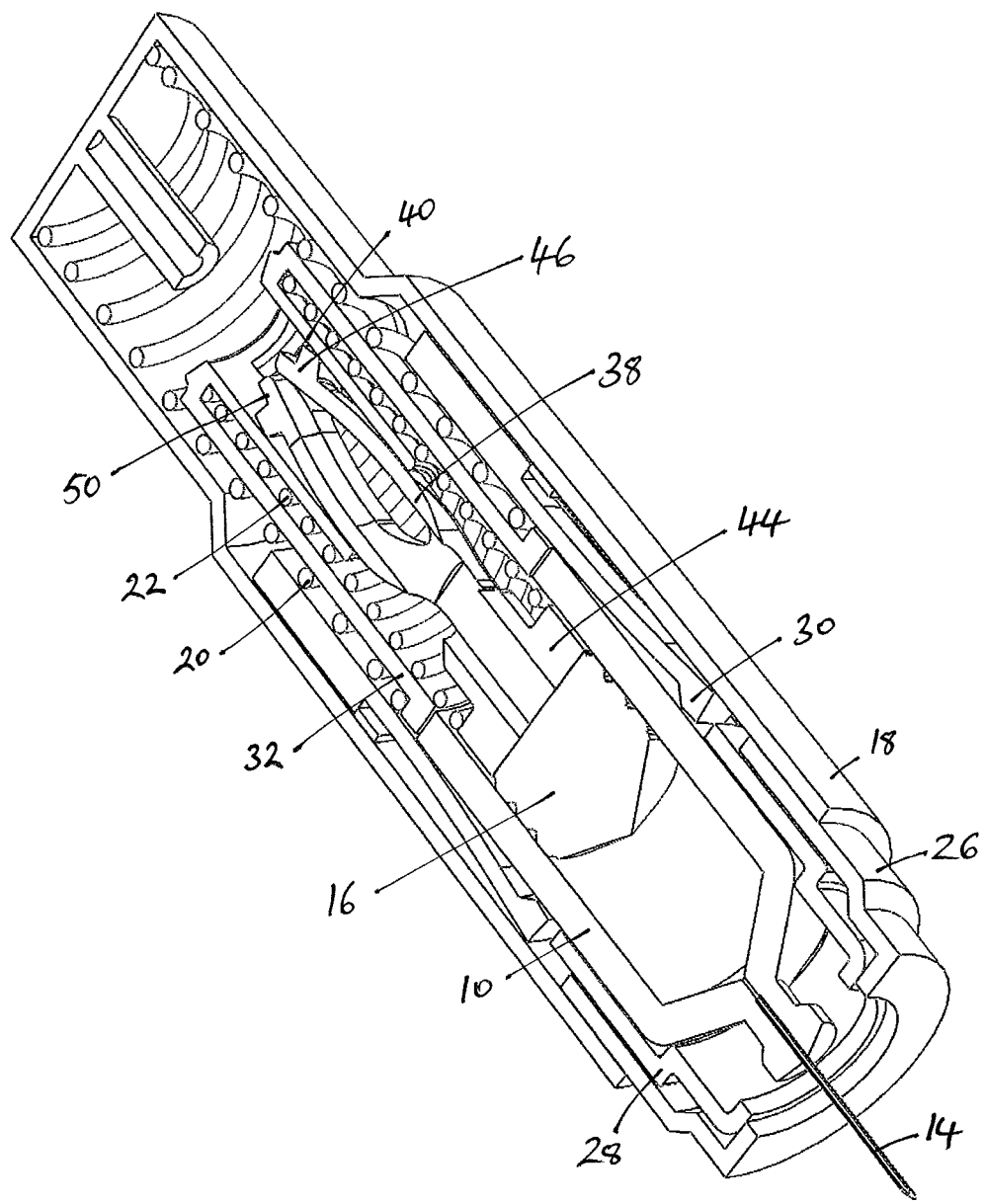
FIG. 5b shows the autoinjector of FIG. 5a from a different perspective.
Figure 8:
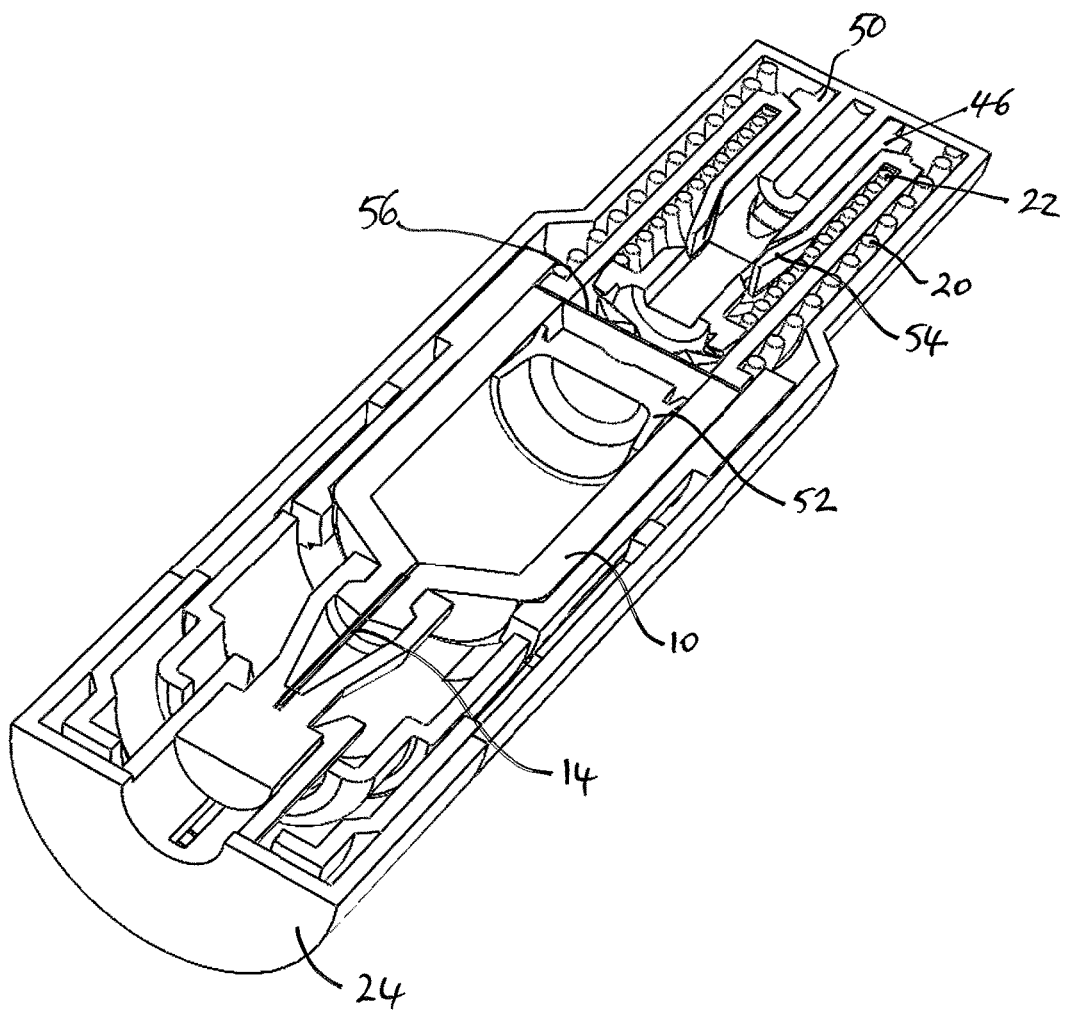
FIG. 8 shows an alternative design of autoinjector to FIG. 1b, incorporating a piercable foil and lowfriction plunger

FIGS. 4a and 4b show the autoinjector in a position when the inner spring 22 has been released and lobes 46 of the inner resilient leg portions 42 are pressed within the outer spring component 32. The front end pusher portion 44 of the inner spring component is driven towards the plunger 16. As illustrated in FIG. 8, a seal 56 may be provided across the back end of the drug container 10 to maintain the drug in pristine condition during storage, and this seal is ruptured by the front end pusher portion 44. The front end pusher portion 44 then engages the plunger 16 and drives it within the drug container to expel the drug, as shown in FIGS. 5a and 5b.

Figure 6A:
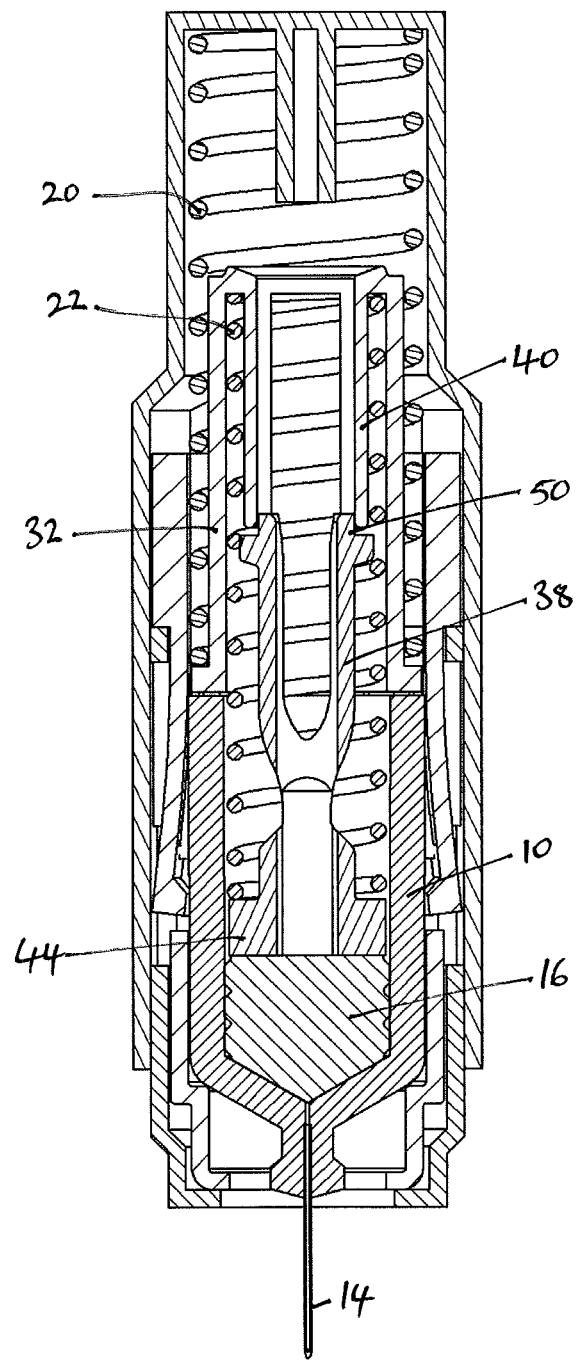
FIG. 6a shows the same autoinjector after the drug has been expelled.
Figure 6B:
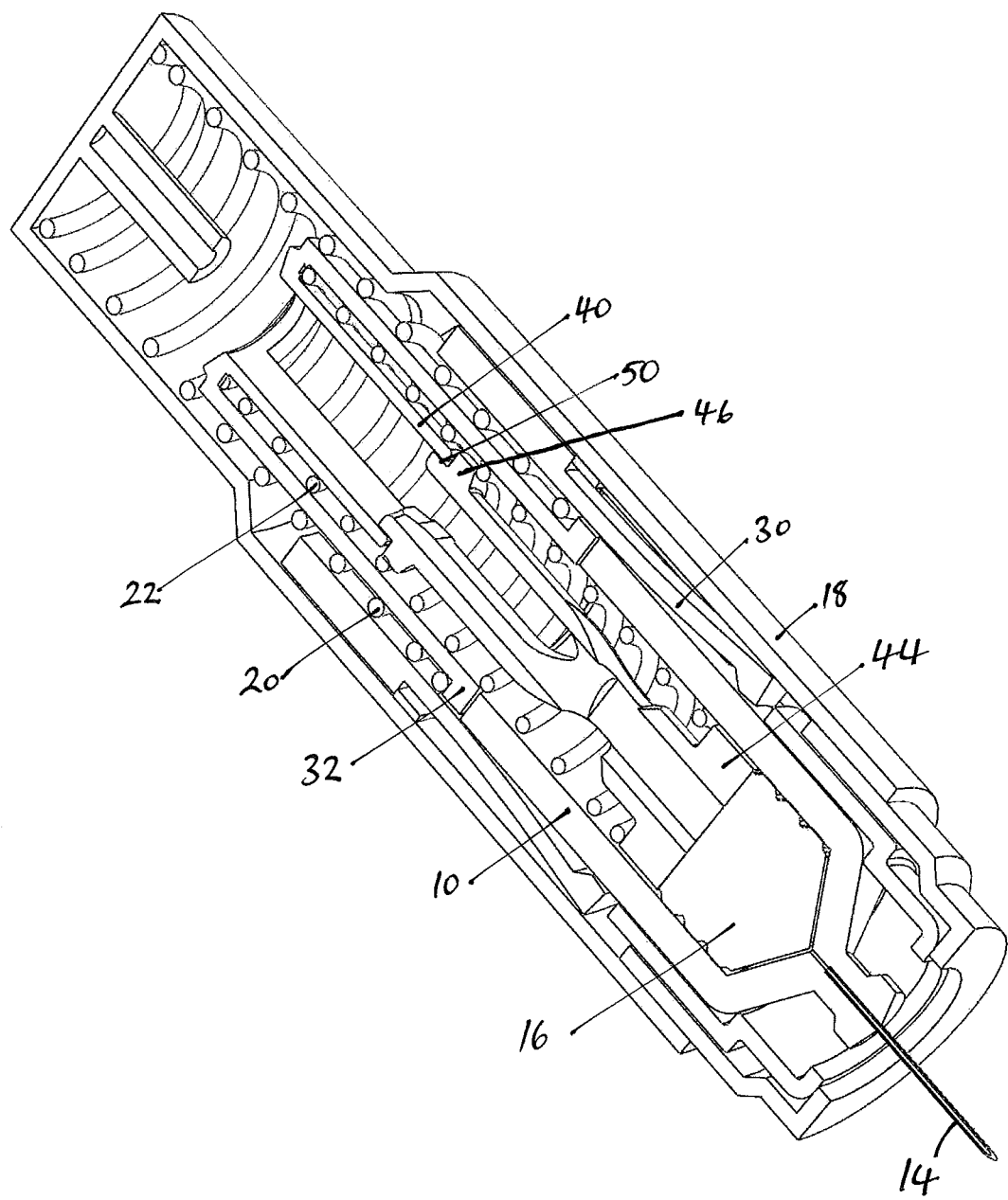
FIG. 6b shows the section view of FIG. 6a from a different perspective.

When the plunger 16 reaches the bottom of the drug container 10, the drug is fully expelled. The leg portions 40 of the outer spring component are dimensioned so that at or just before the point when the plunger reaches the end of its travel, the lobes 46 on the inner spring component 42 are released from the leg portions 40. This release causes the inner resilient arms 42 to expand outwardly from their compressed state, and percussive surfaces 50 on the inner resilient arms above the lobes 46 strike the end of the leg portions 40 to generate an audible sound. This position is illustrated in FIGS. 6a and 6b. The sound indicates to the user that delivery of the drug is complete and that the needle can be withdrawn from the subject.

Figure 7:
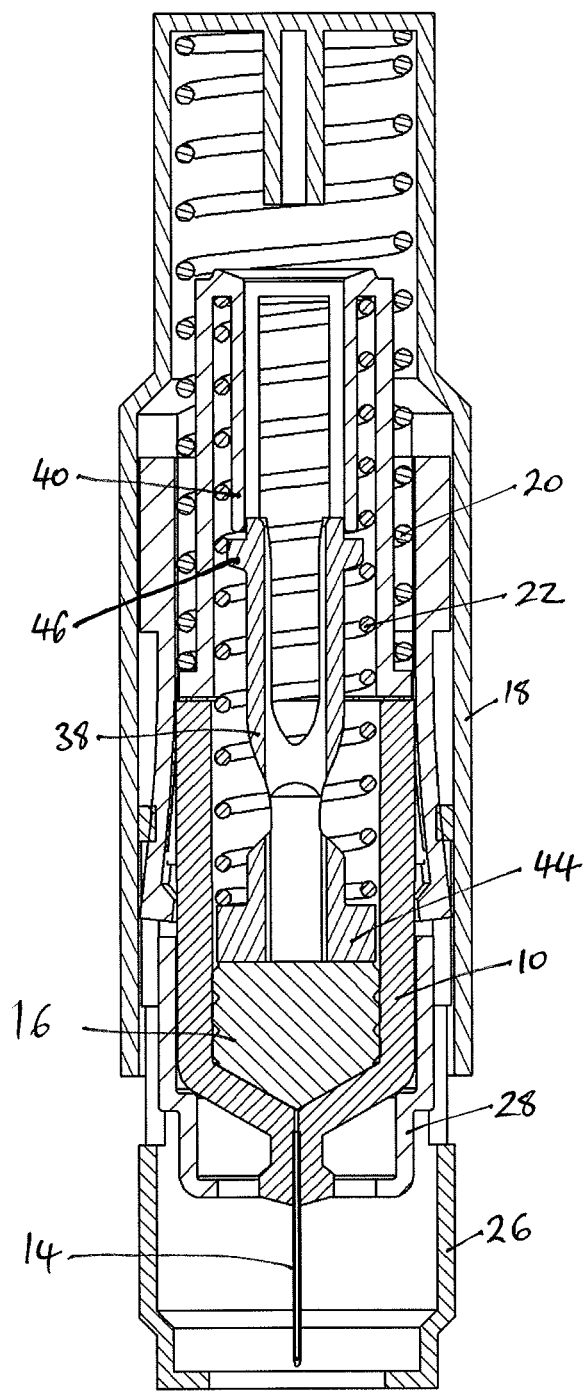
FIG. 7 shows the autoinjector after the drug has been expelled and the autoinjector has been removed from the patient, allowing a needle safety mechanism to extend.

FIG. 7 illustrates the autoinjector after the drug has been expelled and the autoinjector has been removed from the patient, allowing a needle safety mechanism to extend to cover the needle.

The materials used for the housing 18, cap 24, skin sensor 26, front end housing 28, needle insertion latches 30, outer spring component 32 and inner spring component 38 may be plastic, such as EVOH or polyamide, or metal. The inner surface of the drug container must be compatible with the drug and the drug container may be formed from glass or plastic. The various elements described as resilient must have suitable elasticity.

The plunger may be a standard rubber plunger 16 or may be a cup seal plunger 52, as illustrated in FIG. 8. A cup seal plunger, used in conjunction with a back end sealing element 56 which is ruptured by the inner spring component, provides for a more reliable and low friction engagement with the inner wall of the drug container 10. The cup seal plunger may be formed from a substantially nonelastomeric material such as polypropylene, polyethylene or FEP (Fluorinated Ethylene Propylene).

The drive mechanism described with reference to FIGS. 1 to 11 allows for different drive members to be used for needle insertion and for drug expulsion. The release mechanism for the drug expulsion is provided internally of the both the drive means, i.e. the outer and inner springs 20, 22. This allows for compact springs to be used that supply an appropriate force for each stage of drug delivery, and for a compact overall device.

The noise generating mechanism provided by the percussive surface 50 on the inner spring component striking the outer spring component 32 can be reversed or enhanced by forcing a surface on the outer spring component 32 to strike a portion of the inner spring component 38 as, or just before, drug delivery is completed. This can be achieved by forming legs 40 with an inwardly extending lower end 54, as shown in the Figures. When the lobes 46 pass the legs 40, the inwardly extending lower ends 54 are flexed outwardly by the lobes. The ends 54 then snap back to strike the percussive surface 50 once the lobes 46 have passed. However, it should be clear that the noise generating mechanism does not require the lower ends of the legs 40 to be inwardly extending; they may simply be straight, and struck by percussive surface 50 to generate a noise.

Figure 12:
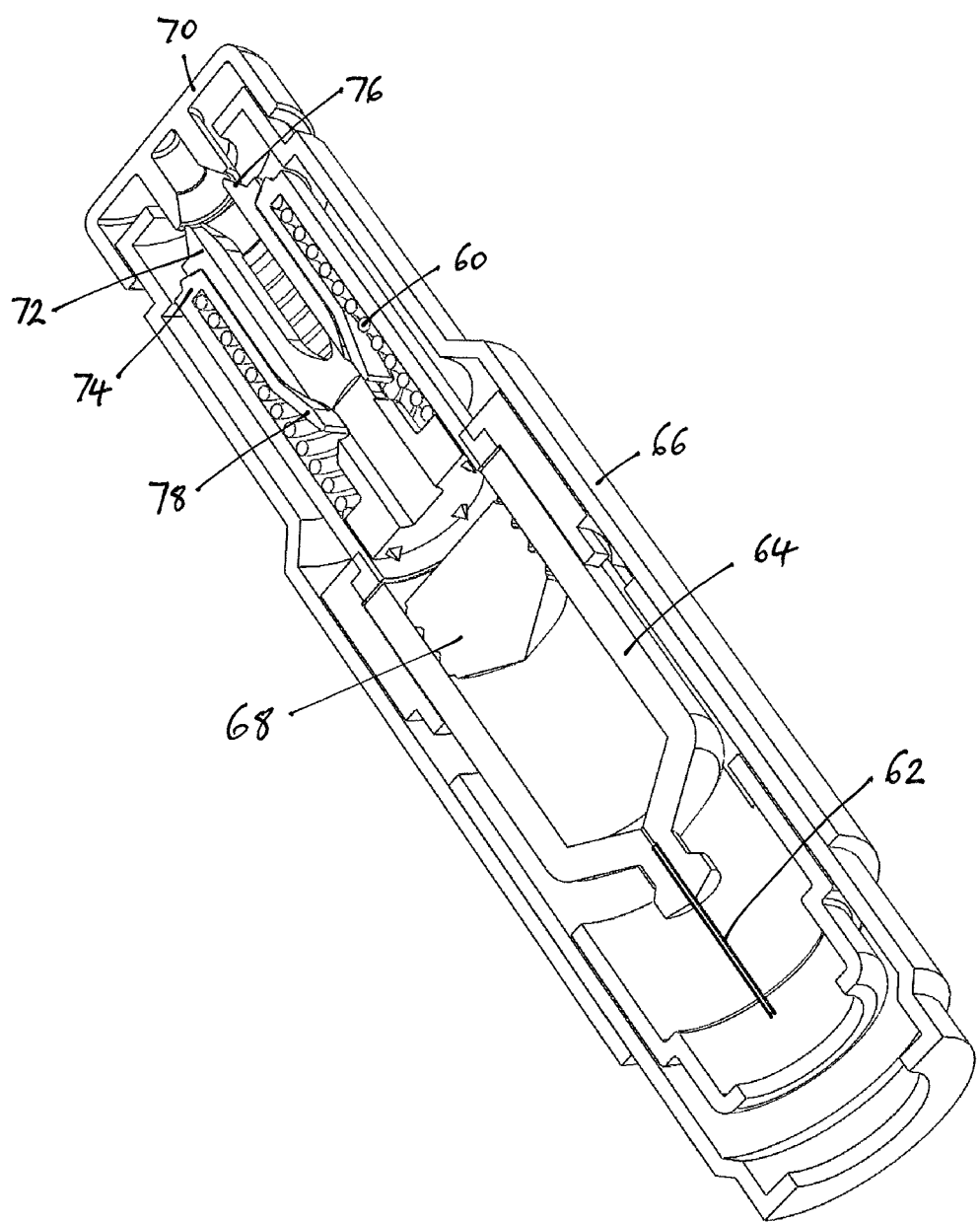
FIG. 12 shows a section view of a second embodiment of an autoinjector having only a single drive spring prior to drug delivery.
Figure 13:
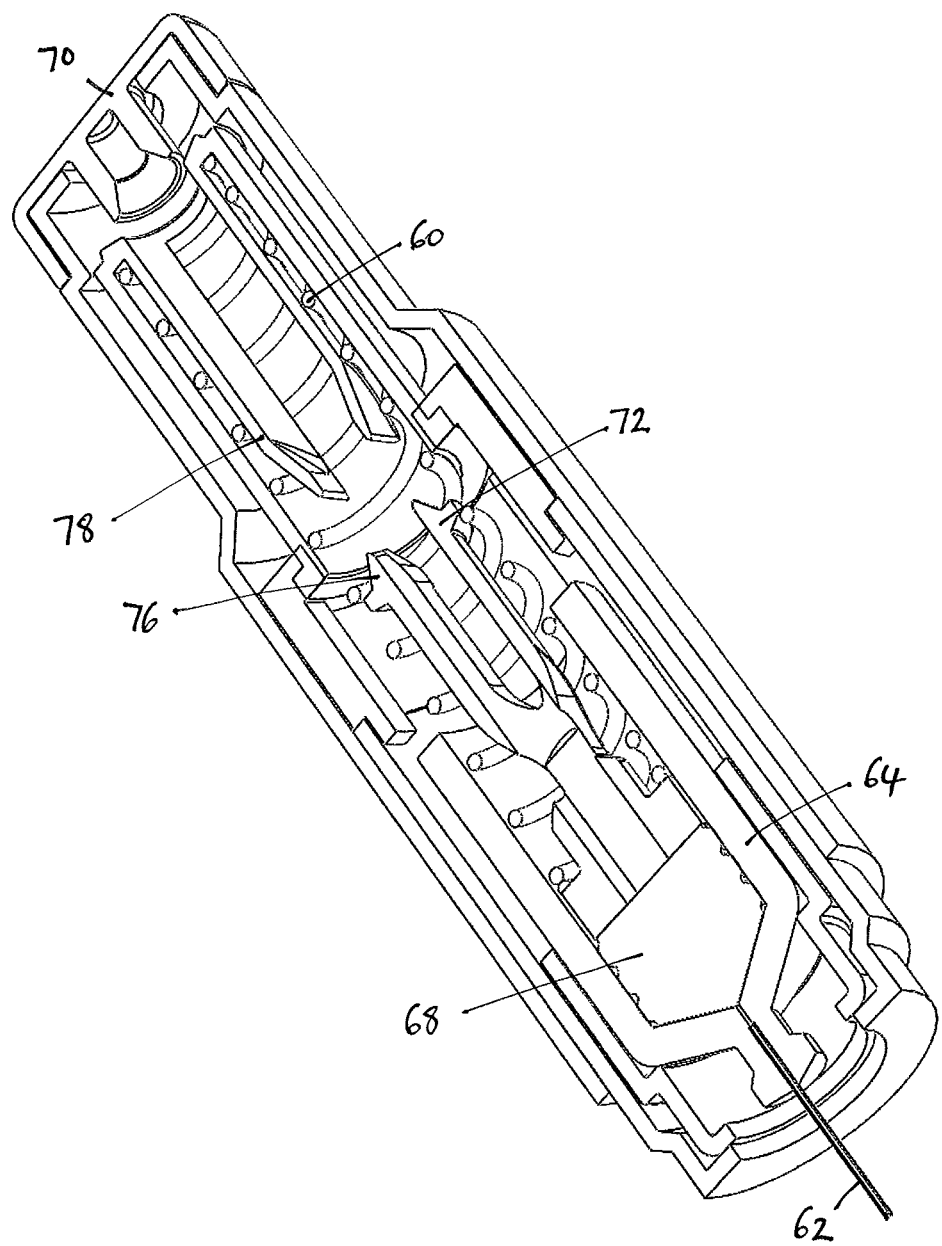
FIG. 13 shows the autoinjector of FIG. 12 after drug delivery.

It should be clear that a noise generating mechanism of this type may also be used in autoinjectors employing only a single drive spring to provide for either or both needle insertion and drug expulsion. This is illustrated in FIGS. 12 and 13. FIG. 12 shows second embodiment of an autoinjector with a single drive spring 60 that drives both a needle 62 and a drug container 64 through a housing 66 for needle insertion and a drives a plunger 68 through the drug container 64 for expulsion of the drug. The drive mechanism is activated by a push button 70 that squeezes spring component 72 to release it from bearing surface 74. The same lobe and percussive surface structure described with reference to the first embodiment is used in this embodiment. As the spring reaches its fullest extension, as shown in FIG. 13, the percussive surfaces 76 strike the end of legs 78 to generate an audible indication to a user that drug delivery is complete.

Figure 14:
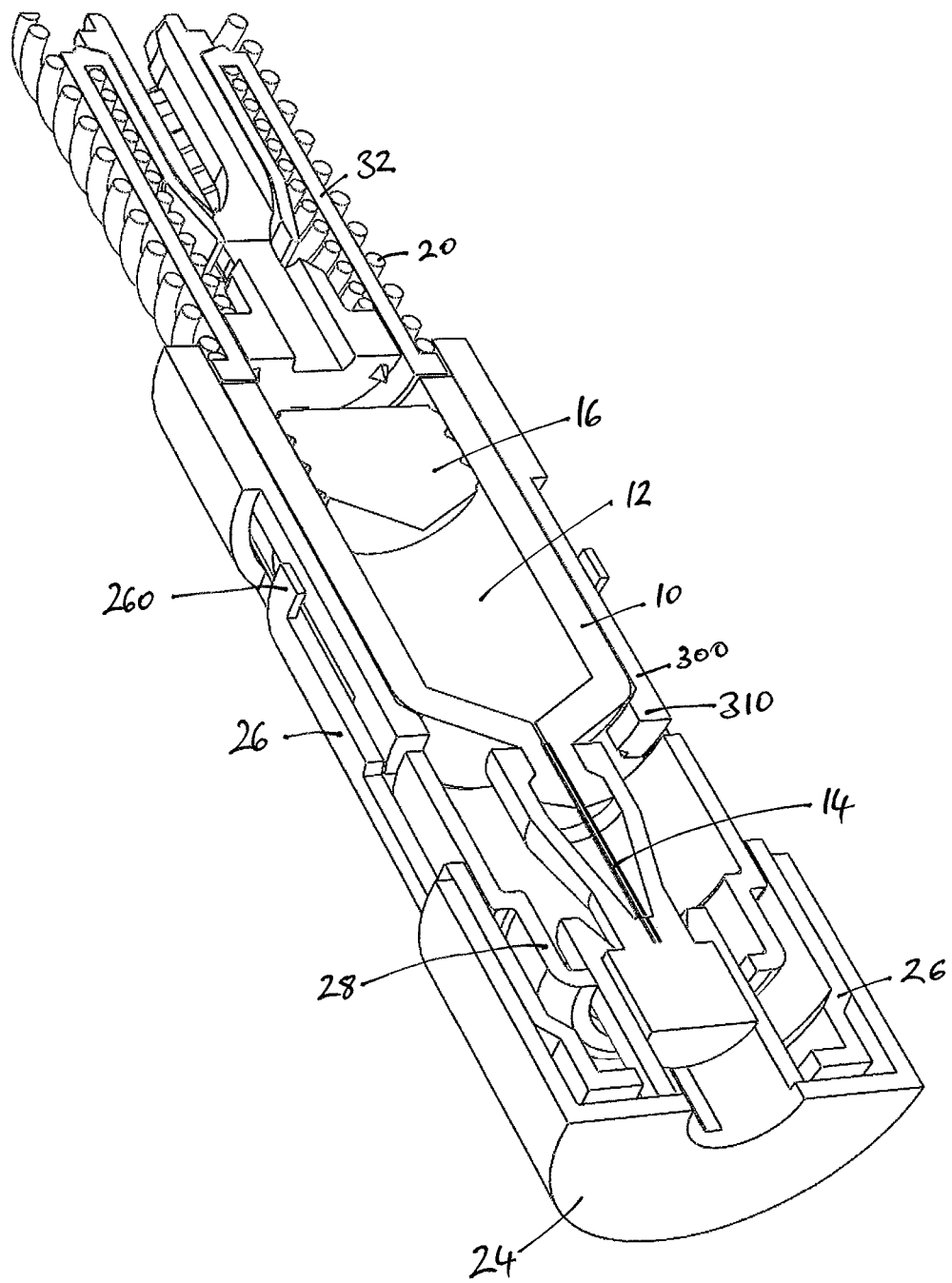
FIG. 14 shows the autoinjector of FIG. 1a from a different perspective, with the housing not shown.

FIGS. 14 to 18 illustrate more clearly the mechanism used to release the outer spring 20 of the first embodiment using the skin sensor 26. FIG. 14 is a view of the autoinjector shown in FIG. 1a from a different perspective, with the main housing 18 removed. FIG. 14 illustrates more clearly that the skin sensor 26 extends to about midway up the drug container 10. The needle insertion latches 30 are resilient arms 300 on which heads 310 are provided. The heads engage the front end of the drug container 10 to retain the outer spring. The latches 30 may be formed as a single moulding with the front end body 24. In the position shown in FIG. 14 heads 310 are held in engagement with the drug container by the skin sensor 26, including skin sensor lugs 260.

Figure 15:
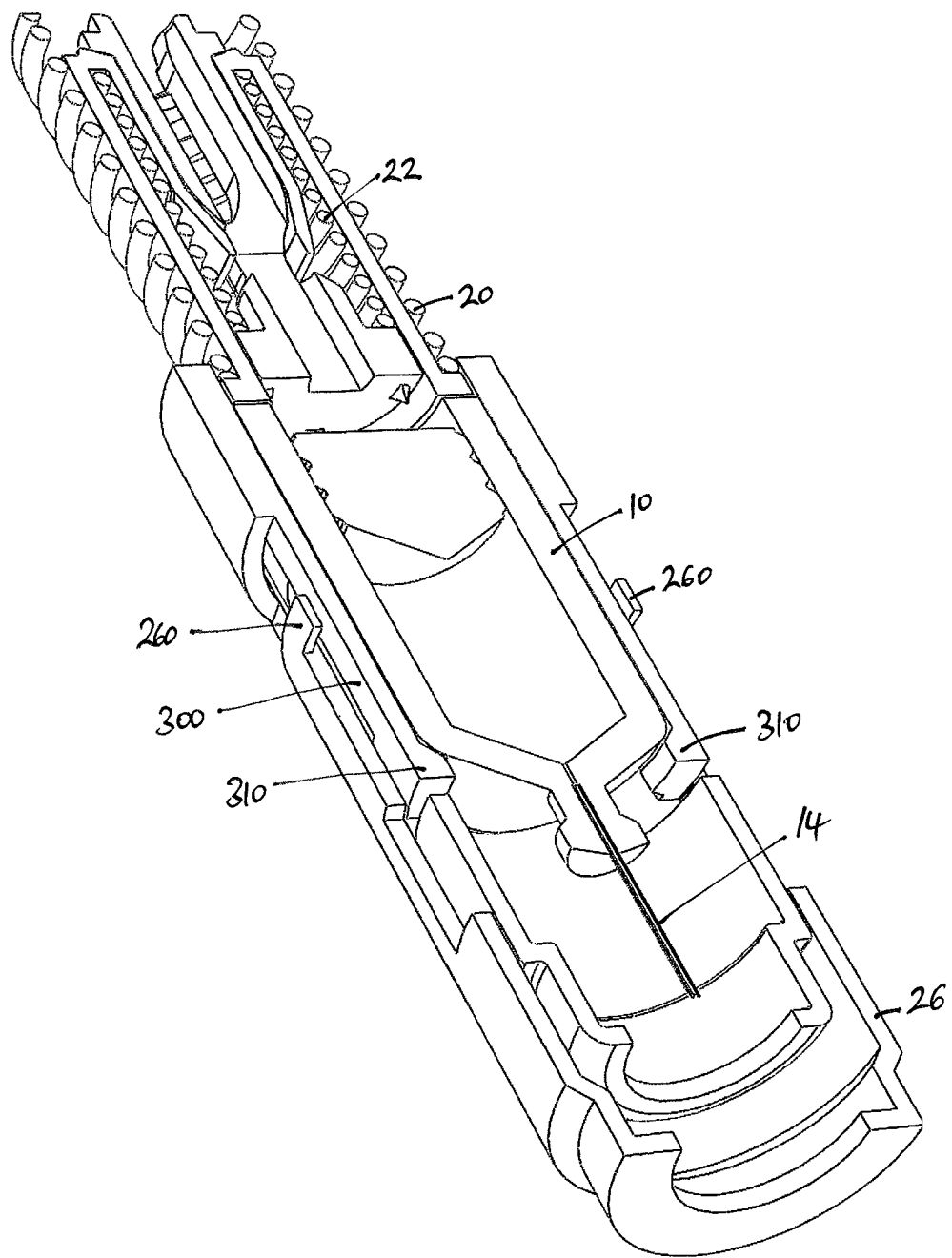
FIG. 15 shows the autoinjector of FIG. 2a from a different perspective with the housing not shown.

FIG. 15 is a view of the autoinjector shown in FIG. 2a from a different perspective, with the main housing 18 removed. The cap 26 has been removed.

Figure 16:
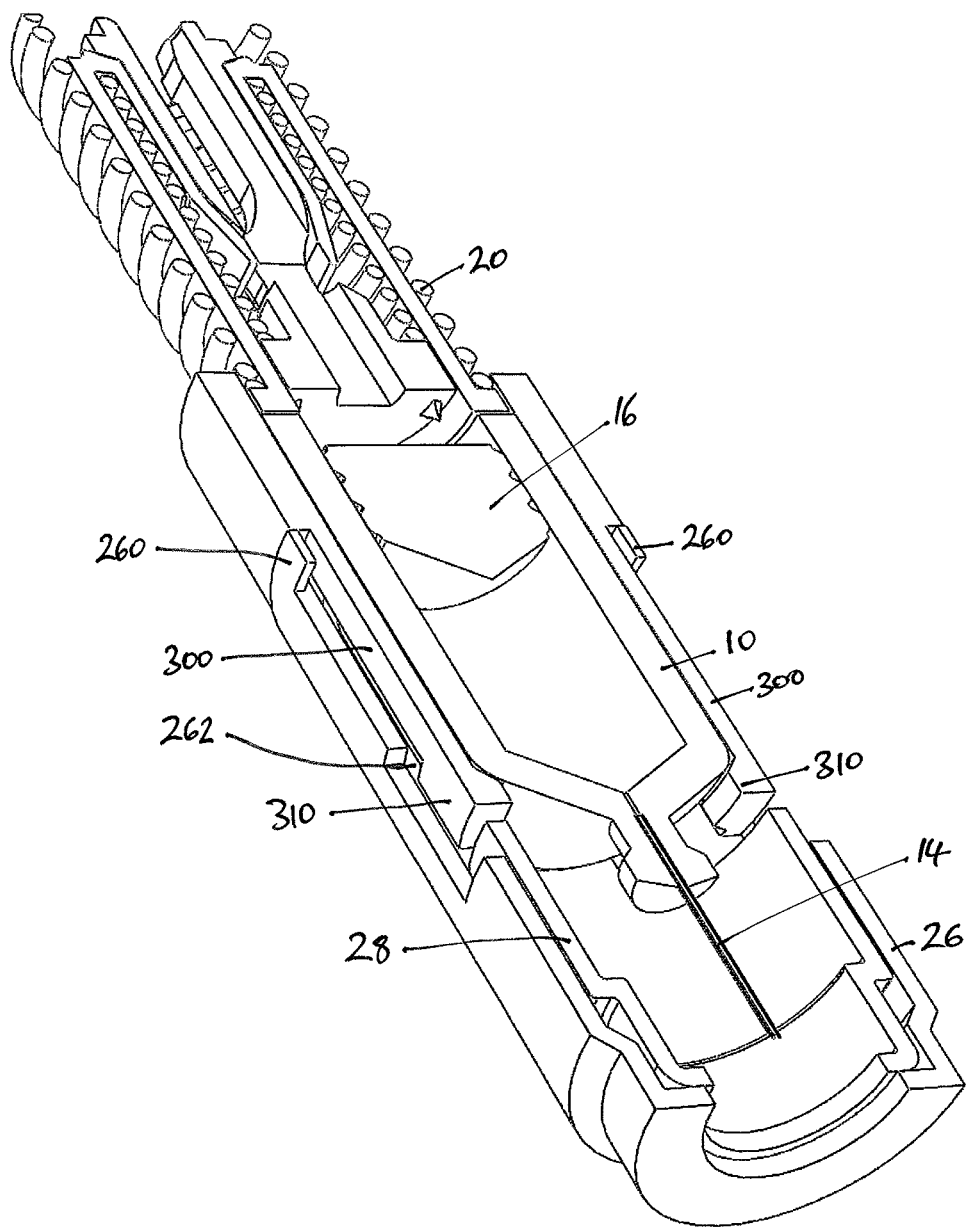
FIG. 16 shows the autoinjector of FIG. 15 with the skin sensor pushed back.

FIG. 16 illustrates the autoinjector of FIG. 15 with the skin sensor moved back as a result of contact with the skin of a patient. The skin sensor has cut out portions 262 that correspond to heads 310 which are moved into alignment with heads 310 in the position shown in FIG. 16.

Figure 17:
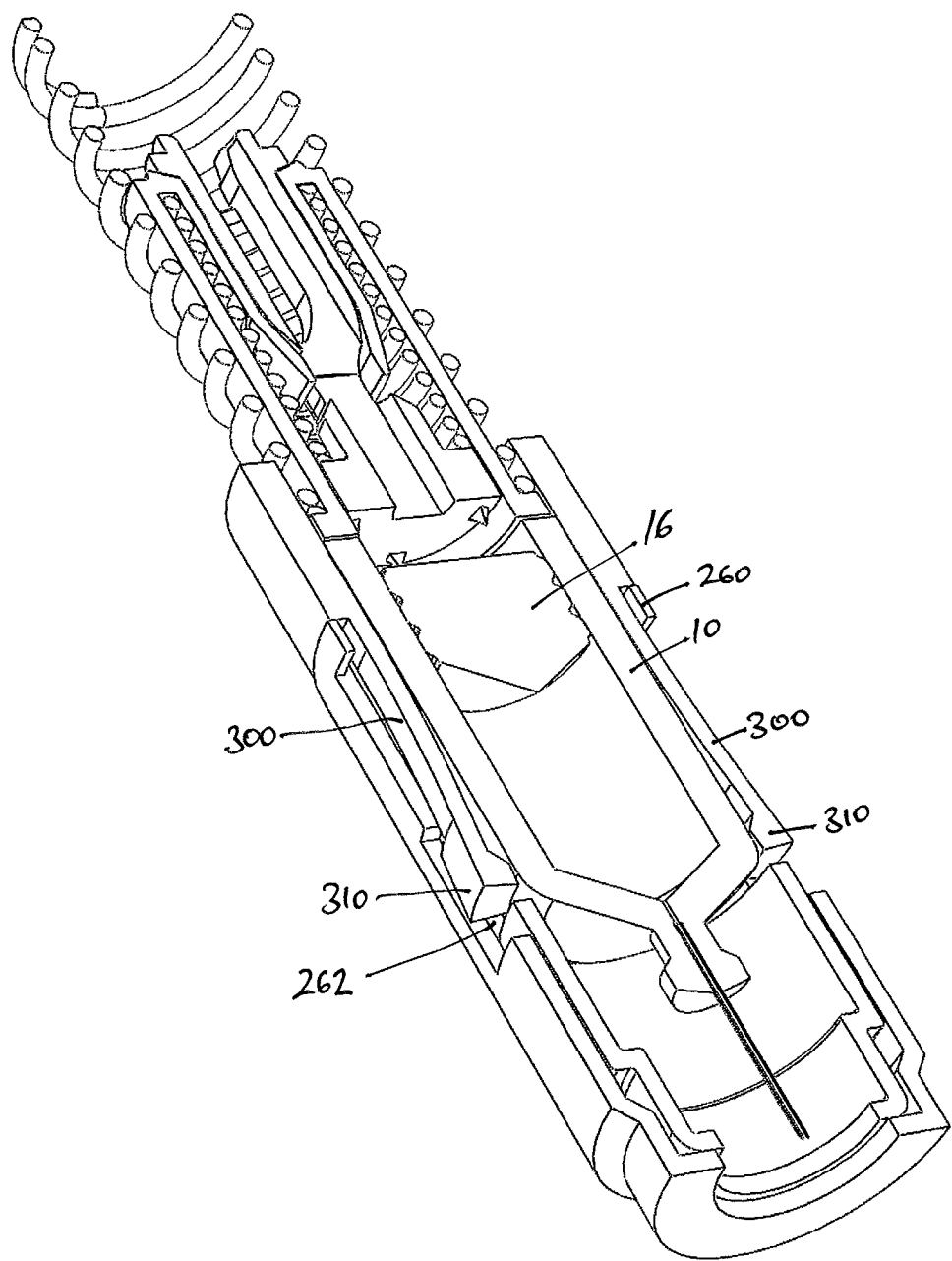
FIG. 17 shows the autoinjector of FIG. 16 a moment later.

FIG. 17 shows the autoinjector of FIG. 16 a moment later. The space provided by cut out portions 262 allow the arms 300 to flex outwardly under the force provided by the outer spring 20 through the drug container 10. The heads 310 are thus moved out of engagement with the front end of the drug container and the drug container 10 can then move forward within the housing to insert the needle 14.

Figure 18:
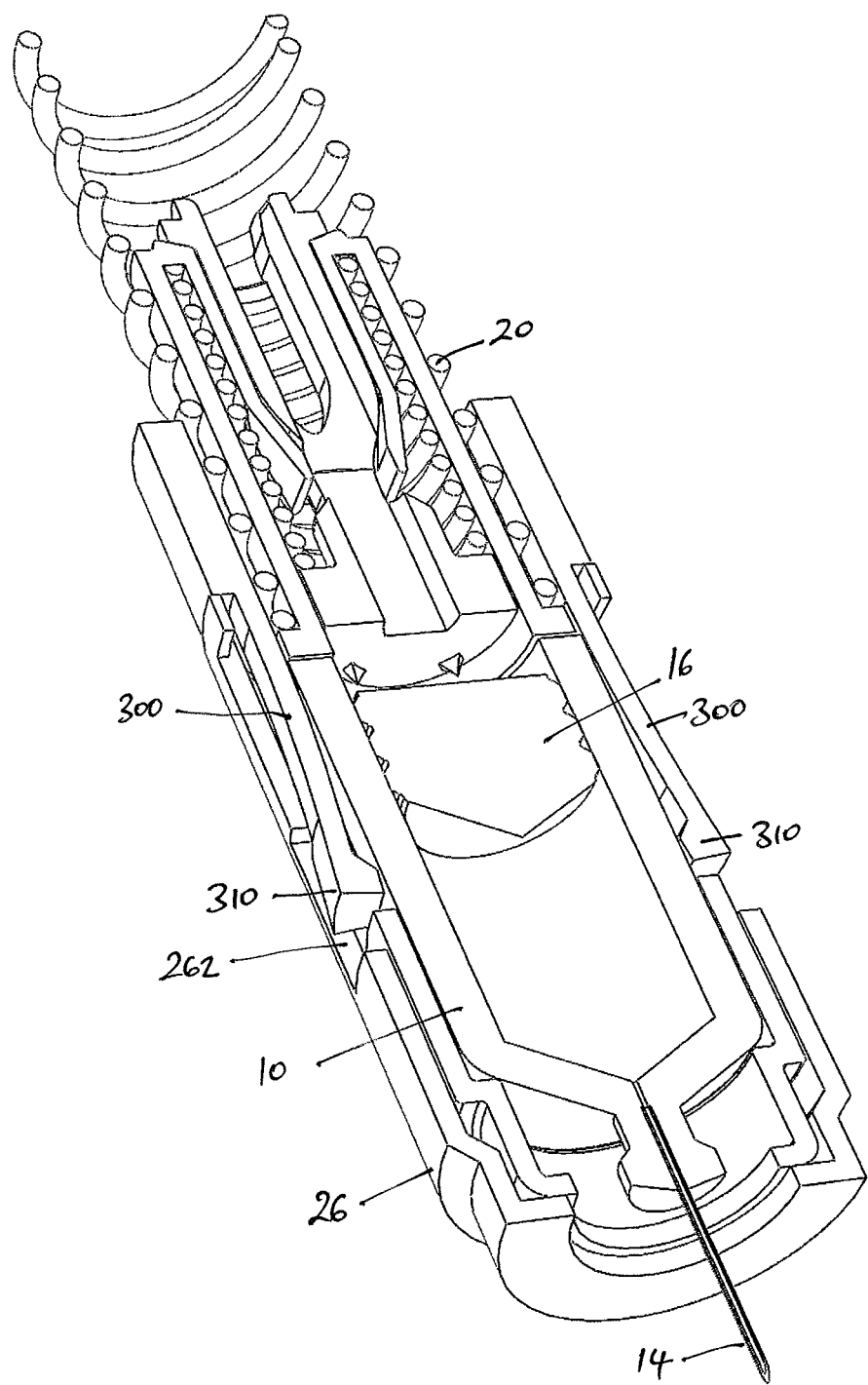
FIG. 18 shows the autoinjector of FIG. 3a from a different perspective with the housing not shown.

FIG. 18 is a view of the autoinjector shown in FIG. 3a from a different perspective, with the main housing 18 removed. In FIG. 18 the outer spring 20 is fully extended and the needle in an inserted position. The arms 300 remain flexed away from the drug container 10, and the heads remain within cut out portions 262.

Again it should be clear that a skin sensor activation mechanism of this type which releases a front end of a drug container to activate a needle insertion mechanism may be used with an autoinjector having only a single drive means for either or both needle insertion and drug expulsion.

The invention claimed is:

1. A delivery mechanism for an autoinjector comprising:
   a first drive member configured to drive a first component,
   a second drive member configured to drive a second component, and
   a release mechanism configured to control a sequence of release of the first drive member and the second drive member, wherein the release mechanism is positioned at least partially within the first or second drive member,
wherein the first drive member is positioned between a main body and the first component, and the second drive member is positioned between the first component and the second component, and
wherein the release mechanism includes
a locking surface, the locking surface being fixed to, or part of, the main body, and
an inner retaining component configured to directly engage the locking surface and retain the second drive member after release of the first drive member until the locking surface is moved a predetermined distance relative to the inner retaining component to disengage the inner retaining component from the locking surface, after which the second drive member is released, and
wherein release of the first drive member moves the inner retaining component relative to the locking surface in order to disengage the inner retaining component from the locking surface and subsequently release the second drive member.

2. The delivery mechanism according to claim 1 wherein the release mechanism is positioned at least partially within both the first and second drive members.

3. The delivery mechanism according to claim 1, wherein the second drive member is positioned at least partially within the first drive member.

4. The delivery mechanism according to claim 1, wherein, in use, one of the first and second drive members is responsible for providing a force to insert a needle into a subject, and the other of the first and second drive members is responsible for providing a force to expel a drug through the needle.

5. The delivery mechanism according to claim 1, wherein the inner retaining component comprises a latch which engages on a bearing surface on the first component.

6. The delivery mechanism according to claim 5, wherein the locking surface maintains the latch in an engaged position with the bearing surface before the first drive member is released.

7. The delivery mechanism according to claim 5, wherein the latch is fixed to or part of the second component.

8. The delivery mechanism according to claim 1, wherein in use the first drive member moves from an initial position before it is released to a final position after it has been released, and the second drive member moves from an initial position before it is released to a final position after it has been released, further comprising a noise-generating mechanism configured to generate a sound when the second drive member has moved to its final position,
wherein the noise-generating mechanism includes two or more surfaces, one of which is caused to strike the other to make the sound substantially at the time that the second drive member reaches its final position.

9. The delivery mechanism according to claim 8 wherein the noise-generating mechanism is positioned at least partially within the first or second drive member.

10. The delivery mechanism according to claim 9 where the noise-generating mechanism is positioned at least partially within both the first and second drive members.

11. The delivery mechanism according to claim 8 wherein one of the surfaces is fixed to or part of the second component.

12. The delivery mechanism according to claim 8 wherein one of the surfaces is fixed to or part of the first component.

13. An autoinjector comprising the delivery mechanism in accordance with claim 1.

14. The delivery mechanism according to claim 1 further comprising:
a housing that includes the main body;
a drug container having a front end coupled to a needle;
a releasable drive mechanism that includes the first drive member and the second drive member, the releasable drive mechanism being coupled to a rear end of the drug container, in use the drive mechanism moving from an initial configuration to a final configuration to move the drug container and needle relative to the housing in order to insert the needle into a subject; and
a releasable locking mechanism retaining the drive mechanism in the initial configuration, the locking mechanism being fixed to the housing and engaging the front end of the drug container.

15. The delivery mechanism according to claim 14, wherein the locking mechanism comprises a resilient arm fixed relative to the housing.

16. The delivery mechanism according to claim 14, wherein the releasable locking mechanism is coupled to a skin sensor configured to sense a skin surface of a patient, wherein the skin sensor comprises a movable element that moves relative to the housing when it is pressed against a skin surface, movement of the movable element releasing the locking mechanism from engagement with the front end of the drug container.

17. The delivery mechanism according to claim 1, further comprising:
a releasable drive mechanism that includes the first drive member and the second drive member, in use the drive mechanism moving from an initial configuration to a final configuration to expel a drug from the autoinjector; and
a noise-generating means coupled to the drive mechanism and configured to generate a sound when the drive mechanism has moved to the final configuration, the noise-generating means being positioned fully within the drive mechanism in use.

18. A delivery mechanism for an autoinjector comprising:
a first drive member configured to drive a first component,
a second drive member configured to drive a second component, and
a release mechanism configured to control a sequence of release of the first drive member and the second drive member, wherein the release mechanism is positioned at least partially within the first or second drive member,
wherein the first drive member is positioned between a main body and the first component, and the second drive member is positioned between the first component and the second component, and
wherein the release mechanism includes
a locking surface, the locking surface being fixed to, or part of, the main body, and
an inner retaining component configured to engage the locking surface and retain the second drive member after release of the first drive member until the locking surface is moved a predetermined distance relative to the inner retaining component to disengage the inner retaining component from the locking surface, after which the second drive member is released,
wherein the locking surface is located within the inner retaining component, and wherein release of the first drive member moves the inner retaining component relative to the locking surface in order to disengage the inner retaining component from the locking surface and subsequently release the second drive member.

* * * * *